(12) United States Patent
Yao et al.

(10) Patent No.: US 9,202,606 B2
(45) Date of Patent: Dec. 1, 2015

(54) FUNCTIONAL NANOSTRUCTURED "JELLY ROLLS" WITH NANOSHEET COMPONENTS

(71) Applicant: University of Georgia Research Foundation, Inc., Athens, GA (US)

(72) Inventors: Kun Yao, Athens, GA (US); Manoj Manjare, Athens, GA (US); Christopher Andrew Barrett, Athens, GA (US); Tina Trnka Salguero, Athens, GA (US); Yiping Zhao, Statham, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 326 days.

(21) Appl. No.: 13/861,618

(22) Filed: Apr. 12, 2013

(65) Prior Publication Data
US 2014/0147473 A1    May 29, 2014

Related U.S. Application Data

(60) Provisional application No. 61/623,719, filed on Apr. 13, 2012.

(51) Int. Cl.
| | |
|---|---|
| *A61K 9/00* | (2006.01) |
| *H01B 1/22* | (2006.01) |
| *H01M 6/40* | (2006.01) |
| *A61K 8/02* | (2006.01) |
| *B82Y 30/00* | (2011.01) |
| *B82Y 40/00* | (2011.01) |

(52) U.S. Cl.
CPC . *H01B 1/22* (2013.01); *H01M 6/40* (2013.01); *A61K 8/0233* (2013.01); *B82Y 30/00* (2013.01); *B82Y 40/00* (2013.01); *Y10T 428/2918* (2015.01); *Y10T 428/2935* (2015.01)

(58) Field of Classification Search
CPC .................................................. A61K 8/0233
See application file for complete search history.

(56) References Cited

U.S. PATENT DOCUMENTS

| | | | | |
|---|---|---|---|---|
| 2010/0330421 | A1* | 12/2010 | Cui et al. | 429/217 |
| 2012/0100203 | A1* | 4/2012 | Fang et al. | 424/443 |

OTHER PUBLICATIONS

Seo J-W, et al. Two-Dimensional Nanosheet Crystals. Nanostructures. Angew. Chem. Int. Ed. 2007, 46, 8828-8831.

* cited by examiner

*Primary Examiner* — Paul Dickinson
(74) *Attorney, Agent, or Firm* — Thomas|Horstemeyer, LLP

(57) ABSTRACT

The present disclosure relates to multilayered materials that are designed to roll spontaneously into micron-sized, cylindrical "jelly roll" or scroll structures. Specifically in this disclosure, at least one of the layers is comprised of a nanosheet material.

4 Claims, 24 Drawing Sheets

A                          B

US 9,202,606 B2

FUNCTIONAL NANOSTRUCTURED "JELLY ROLLS" WITH NANOSHEET COMPONENTS

CROSS-REFERENCE TO RELATED APPLICATION

This application claims priority to U.S. provisional application entitled "Functional Nanostructured 'Jelly Rolls' with Nanosheet Components," having Ser. No. 61/623,719 filed on Apr. 13, 2012, which is entirely incorporated herein by reference.

STATEMENT REGARDING FEDERALLY SPONSORED RESEARCH OR DEVELOPMENT

This invention was made with Government support under grant number ECCS-0901141, awarded by the U.S. National Science Foundation. The Government has certain rights in this invention.

BACKGROUND

Recent work on controlling the three-dimensional morphology of nano- and micro-sized objects has included an increasing number of studies on scrolls. The scroll form is attractive because it is a structure with open ends and edges, adjustable interlayer distances, and flexible interior volume that can be used for cargo transport. Some nanostructured heterolayer systems are known to exhibit scrolling behavior, and the major efforts have involved metal and metal oxide (especially semiconductor) multilayers deposited on a sacrificial material layer. Upon etching (removing the sacrificial layer), the released heterostructures spontaneously roll into micrometer-sized scrolls/tubes. However, new materials and new techniques to fabricate such functional nano- and micro-sized scrolls need to be explored to extend the application and lower the cost.

SUMMARY

Embodiments of the present disclosure, in one aspect, relate to functionalized nanostructured scrolls and methods of making functionalized nanostructured scrolls.

Briefly described, embodiments of the present disclosure include a method of making a functionalized multilayer micron-sized scroll structure comprising depositing an aqueous solution of nanosheets onto a substrate, coating the nanosheet layer with a first layer of a material to form a multilayer structure using vapor deposition, where the first layer comprises a metal containing substance selected from a pure metal, a metal oxide, a metal nitride, a metal oxynitride, a metal carbide, and a combination thereof, adding a solvent, and sonicating the multilayer material so that the multilayer material spontaneously forms a functionalized multilayer micron-sized scroll structure.

Embodiments of the present disclosure further include a functionalized multilayer micron-sized scroll structure comprising a first layer, where the first layer comprises a nanosheet where the nanosheet comprises a material selected from graphene oxide (GO), graphene, $MoS_2$, hexagonal boron nitride (BN), and a combination thereof, and a second layer, where the second layer comprises a material selected from Ti, Pt, Fe, Ni, $TiO_2$, $Fe_2O_3$, Si, and a combination thereof, where the first layer and the second layer roll spontaneously to form the multilayer micron-sized scroll structure, and where the scroll structure is open at both ends and hollow in the center.

Embodiments of the present disclosure include a method of using a functionalized multilayer micron-sized scroll structure selected from surface enhanced Raman spectroscopy (SERS), batteries, drug loading, drug delivery, hydrogen storage, catalytic reaction, and a combination thereof.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
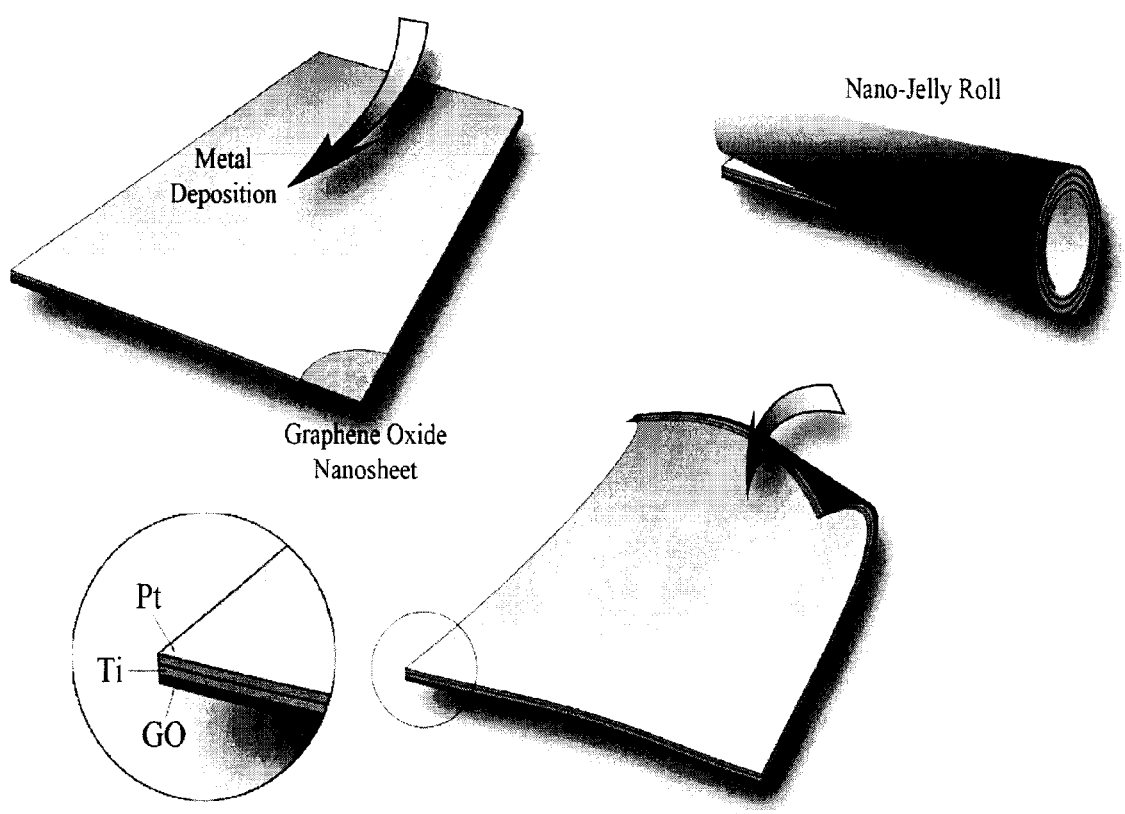
FIG. 1 is a schematic illustrating a multilayer material that can roll-up into a "jelly roll" like structure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DISCUSSION

In accordance with the purpose(s) of the present disclosure, as embodied and broadly described herein, embodiments of the present disclosure, in one aspect, relates to multilayered materials that are designed to roll spontaneously into micron-sized, cylindrical "jelly roll" or scroll structures. In an embodiment, at least one of the layers comprises a nanosheet material, which is defined as being at least a single monolayer thick, preferably no more than 10 nm thick, and at least 100 nm in lateral dimensions.

An illustrative example of the present disclosure is shown in FIG. 1. In the initial flat trilayer material, the bottom layer is comprised of graphene oxide (GO) nanosheets, the middle layer is comprised of titanium metal, and the top layer is comprised of platinum metal. When rolled in a scroll-like fashion, the material forms a jelly roll structure that is hollow in the center.

The present disclosure includes bilayer, trilayer, and more complex multilayer structures. At least one of these layers is comprised of a nanosheet material; examples include but are not limited to graphene oxide, graphene, $MoS_2$, and hexagonal BN in the nanosheet morphology. The nanosheet layer is about sub-nm to about several nm in thickness. The subsequent layers typically are comprised of various vapor-deposited materials about several nm in thickness; examples include, but are not limited to, metals, such as Ti, Pt, Fe, Ni, etc or nonmetals, such as $TiO_2$, $Fe_2O_3$, Si, etc. The thicknesses of each layer can be varied independently.

The selection of specific materials for the multilayer scroll structure of the present disclosure is important for at least two reasons. The first reason is that the material properties lead to the creation of interfacial strain and differences in surface energy that promote spontaneous rolling. Another reason is that each material can have a functional contribution as well as a structural contribution. For example, in a graphene oxide/Ti/Pt system, the Pt can act as a catalyst for the decomposition of hydrogen peroxide, which produces bubbles of oxygen gas that can propel the jelly roll forward. Likewise, in a graphene/Ti/Pt system the electrical conductivity function of the graphene layer can be taken advantage of.

After fabrication of the multilayer material on a substrate (e.g., Si wafer), multimicron-sized areas are released in solvents (e.g., water, water based solution, organic solvents) from the substrate by the use of sonication. The solvents with different surface tensions can be used to precisely control the diameter and the quality of the rolls (e.g., cylinders, scrolls). These multilayer materials spontaneously roll up into the scroll structure shown in FIG. 1.

Embodiments of the present disclosure include a functionalized multilayer micron-sized scroll structure comprising a first layer, where the first layer comprises a nanosheet where the nanosheet comprises a material selected from graphene oxide (GO), graphene, $MoS_2$, hexagonal boron nitride (BN), and a combination thereof, and a second layer, where the second layer comprises a material selected from Ti, Pt, Fe, Ni, $TiO_2$, $Fe_2O_3$, Si, and a combination thereof, where the first layer and the second layer roll spontaneously to form the multilayer micron-sized scroll structure, and where the scroll structure is open at both ends and hollow in the center.

Embodiments of the present disclosure include a functionalized multilayer micron-sized scroll structure further comprising a third layer, where the third layer comprises a material selected from the Ti, Pt, Fe, Ni, $TiO_2$, $Fe_2O_3$, Si, and a combination thereof. In an embodiment, the first layer comprises a graphene oxide (GO) nanosheet, the second layer comprises titanium (Ti), and the third layer comprises platinum (Pt), and the Pt layer comprises the innermost layer located within the interior of the scroll structure, and the GO layer comprises the outermost layer of the scroll structure. In another embodiment, the nanosheet is at least a single monolayer thick, and wherein the nanosheet layer is about 0.5 to 3.0 nm in thickness. In an embodiment, the nanosheet layer is about sub-nm to about several nm in thickness. Prior to spontaneously rolling, the GO nanosheet, Ti layer, and Pt layer form a three-layer sandwich-like structure.

Embodiments of the present disclosure include a functionalized multilayer micron-sized scroll structure further comprising at least one additional layer, where the second layer, the third layer, and the at least one additional layer are each at least about 1 nm thick. In another embodiment, the thickness is between about 10 nm to 50 nm, though, depending on the material, it can be greater than about 50 nm.

Embodiments of the present disclosure include a functionalized multilayer micron-sized scroll structure where the structure acts as a microjet engine in the presence of $H_2O_2$ due to a reaction between the Pt layer and the $H_2O_2$ to form $O_2$. In an embodiment, the structure moves at a constant speed of about 85 to 975 $\mu m\ s^{-1}$.

Embodiments of the present disclosure include a functionalized multilayer micron-sized cylindrical structure where the structure is about 0.5 to 5 microns in diameter and about 3 to 40 microns in length. However, these values also depend on what material is used to form the scrolls.

Embodiments of the present disclosure include a method of making a functionalized multilayer micron-sized scroll structure comprising depositing an aqueous solution of nanosheets onto a substrate (e.g., silicon), coating the nanosheet layer with a first layer of a material to form a multilayer structure using vapor deposition, where the first layer comprises a metal containing substance selected from a pure metal, a metal oxide, a metal nitride, a metal oxynitride, a metal carbide, and a combination thereof, adding a solvent, and sonicating the multilayer material so that the multilayer material spontaneously forms a functionalized multilayer micron-sized scroll structure. In an embodiment, the nanosheet comprises a material selected from graphene oxide (GO), graphene, $MoS_2$, hexagonal boron nitride (BN), and a combination thereof. In another embodiment, the nanosheet comprises GO and the first layer comprises Si. In another embodiment, the first layer comprises a material selected from Ti, Pt, Fe, Ni, $TiO_2$, $Fe_2O_3$, Si, and a combination thereof. In an embodiment, the metal can include, but is not limited to, silver, nickel, aluminum, silicon, gold, platinum, palladium, titanium, copper, cobalt, zinc, other transition metals, composites thereof, oxides thereof, nitrides thereof, silicides thereof, phosphides ($P^{3-}$) thereof, oxynitrides thereof, carbides thereof, and combinations thereof.

Embodiments of the present disclosure include a method where the multilayer material spontaneously forms a scroll structure by a detachment mechanism comprising a physical delamination process.

Embodiments of the present disclosure include a method further comprising depositing a second layer of material on the first layer of material prior to adding the solvent. In an embodiment, the second layer is comprised of a material selected from Ti, Pt, Fe, Ni, $TiO_2$, $Fe_2O_3$, Si, and a combination thereof. In another embodiment, the nanosheet comprises GO, the first layer comprises Ti, and the second layer comprises Pt. In another embodiment, the first layer is about 10 nm thick, and the second layer is about 10 to 25 nm thick.

Embodiments of the present disclosure include a method where the multilayer material is sonicated for less than about one minute in 18 MΩ aqueous solution.

Embodiments of the present disclosure include a method further comprising depositing at least one additional layer on the second layer prior to adding the solvent. In an embodiment, the method further comprises immersing the functionalized multilayer micron-sized scroll structure in $H_2O_2$ to form microjet multilayer micron-sized scroll structures.

Embodiments of the present disclosure include a multilayer material where the material exhibits qualities selected from electrical conductivity, strength, flexibility, hydrophobicity, and a combination thereof. In an embodiment, the material is used in catalytic jet engines.

Embodiments of the present disclosure include a multilayer material where the second layer comprises Au, and the "jelly roll" is used for surface enhanced Raman spectroscopy (SERS). In an embodiment, the second layer comprises Si, and the "jelly roll" is used for batteries.

EXAMPLES

Example 1

Example 1A

Graphene Oxide/Si

Figure 4A:
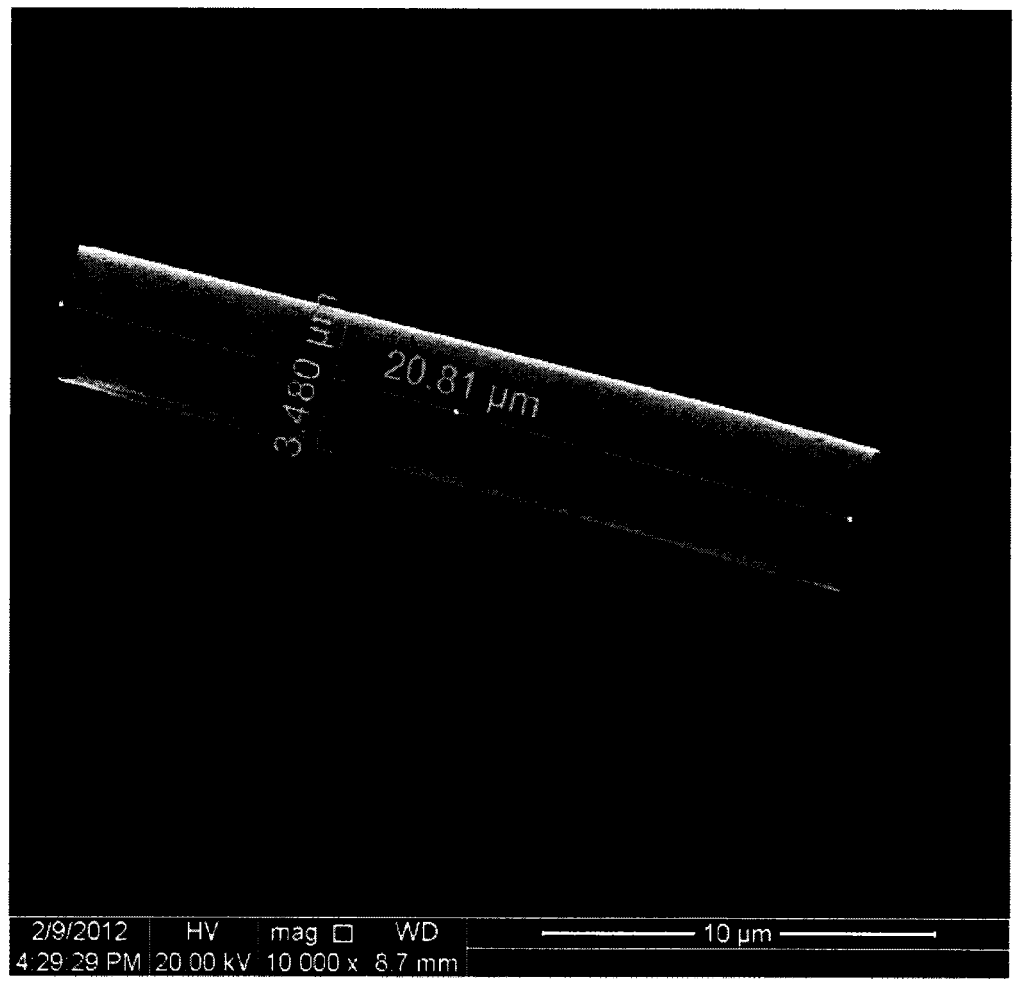
FIGS. 4A-4B are SEM images of graphene-oxide/Si jelly rolls.
Figure 4B:
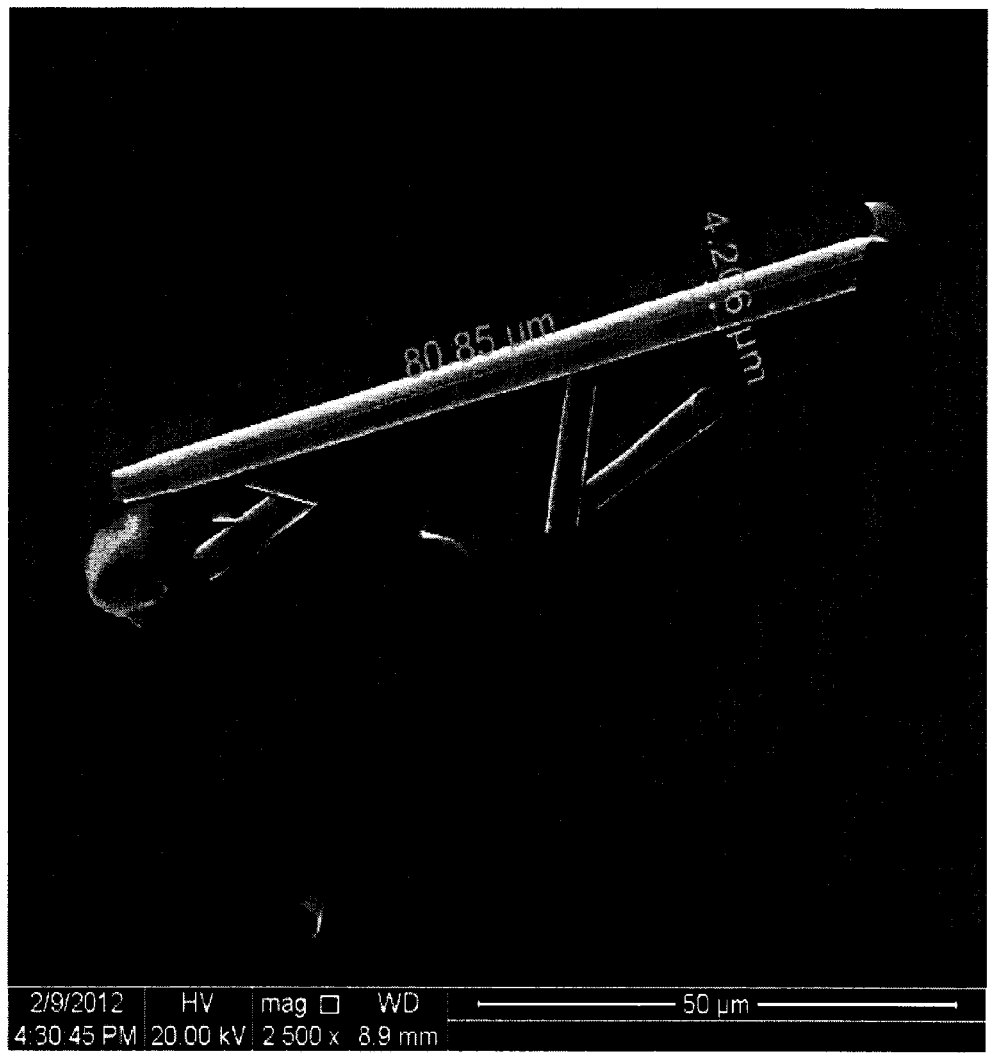

The same strategy shown in Example 1A was followed, but only deposit a 20 nm layer of Si onto the graphene oxide nanosheets. After sonication in water, the two-layer structures also form jelly rolls as shown in FIG. 4.

Previous studies have established that nanosheet materials can roll up spontaneously into nanotube or nanoscroll structures (e.g., graphene, titania, kaolinite, hexaniobate). Other studies have established that certain multilayer materials can roll up spontaneously into micron-sized tube or scroll structures (e.g., $V_2O_5$, Pt/Au/Fe/Ti, InGaAs/GaAs/Cr/Pt). In addition, manually-rolled multilayer systems have been reported.

The nanosheet component of the present disclosure affords several advantages. Because many nanosheet materials can be manipulated as colloidal dispersions, they are easy to deposit via solution-based approaches. In addition, they are convenient starting materials for ultrathin (<about 5 nm), continuous layers down to a single atomic layer. Furthermore, several nanosheet materials have remarkable material properties and/or chemical functionalities that can be incorporated into the jelly roll system (e.g., electrical conductivity, strength, flexibility, hydrophobicity). Last, the deposition of different materials on top of the nanosheets make the sheet structure heterogenous, with different chemical and physical properties on two sides of the surfaces. This allows a great leverage to engineer the sheet materials for different applications.

Applications

An advantage of the jelly roll/scroll morphology is that the ends of the structure are open, in contrast to closed-tube structures. This feature makes it possible to put additional components inside, or to move components from the inside to the outside or vice versa. Many potential applications could utilize these features, such as gas storage and drug loading/delivery systems. In addition, there is growing interest in nano- and micro-level propulsion (that requires the release of gases), which has been demonstrated with the jelly roll structures in this disclosure.

With alternative metal layers, such as gold or silver, the jelly roll structures of the present disclosure may be used for surface enhanced Raman spectroscopy (SERS). In addition, with alternative nonmetal layers, such as Si, the multilayer structure of the jelly rolls also suggests that they have potential for micron-sized, nano-structured batteries and supercapacitors. Further applications may include water or ion channels and sensor applications and advanced photocatalytic materials for solar energy based applications (solar cells, water splitting, $CO_2$ conversion).

Example 1B

Graphene Oxide/Titanium/Platinum

Figures 2A, 2B, 2C, 2D:
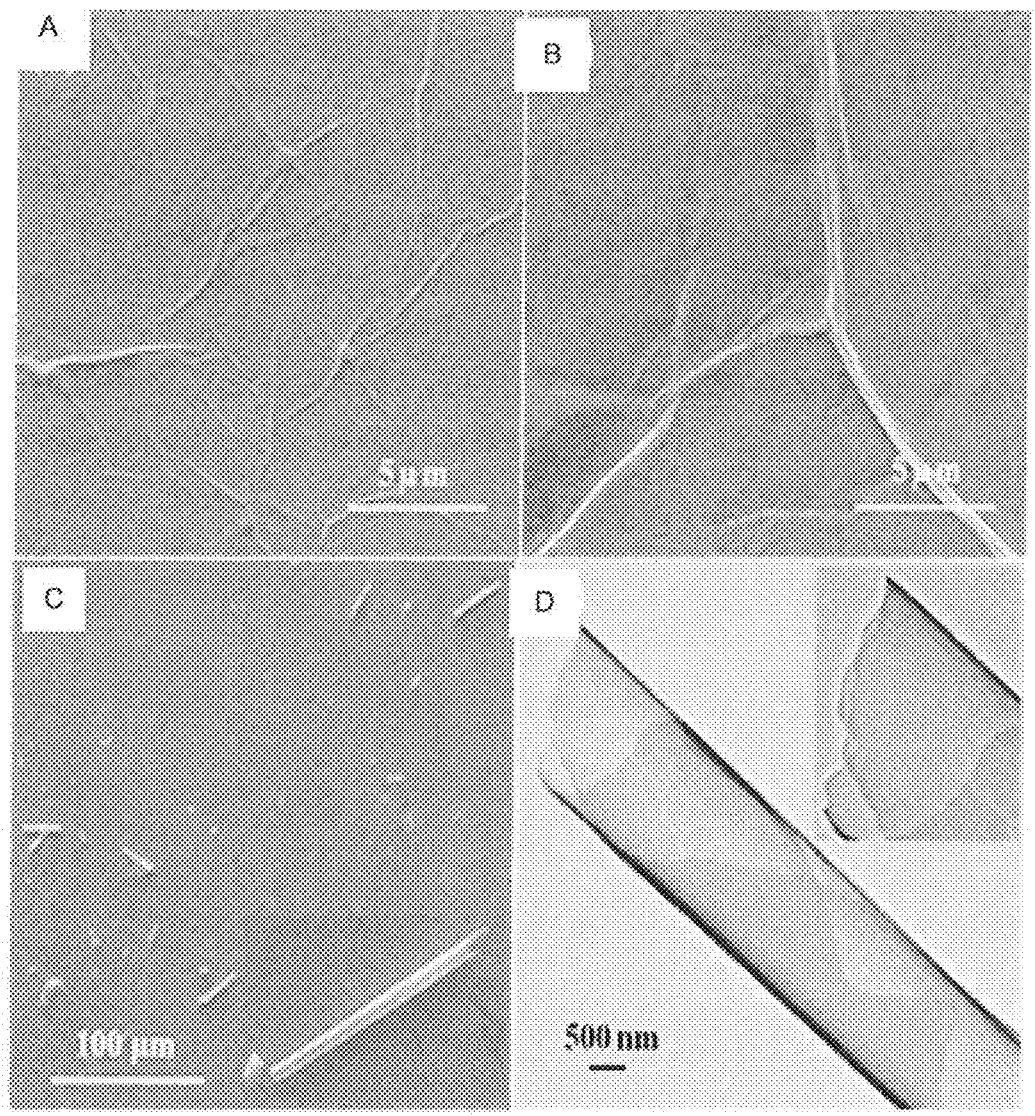
FIGS. 2A-2D are SEM images of graphene oxide sheets on Si before Ti/Pt coating (a), after Ti/Pt coating (b), and jelly rolls after sonication (c). A magnified SEM image of an individual scroll is shown in the inset of 2(c). TEM image of a jelly roll is shown in (d), and the inset shows a magnified image.
Figure 2F:
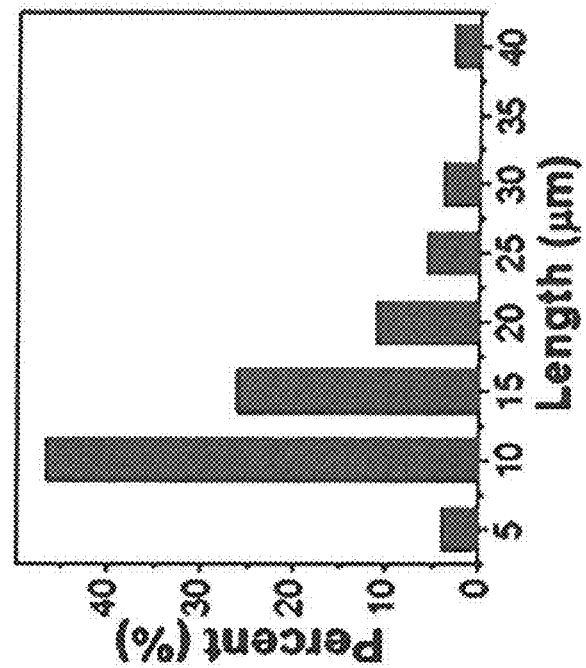
FIGS. 2E-2F are graphs that illustrate the data in (e) and (f) show the size distribution of over 70 graphene oxide-Ti—Pt jelly rolls.
Figure 2E:
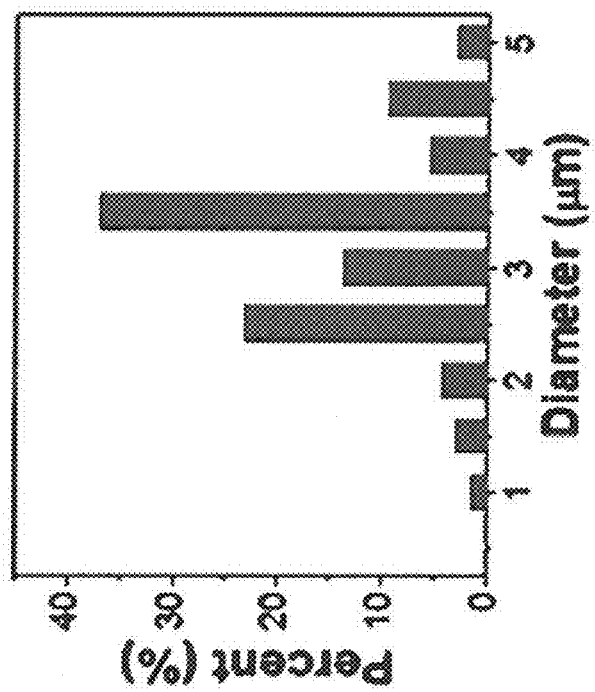

First an aqueous solution of graphene oxide nanosheets was deposited onto a silicon substrate and then coated with thin layers of Ti and Pt (about 10 nm each) using an electron-beam evaporation system. FIGS. 2A and 2B show SEM images of the graphene oxide nanosheets before and after Ti/Pt coating. Although it is difficult to observe the graphene oxide because of poor image contrast, the folds clearly show the existence of large nanosheets. Notably, there are no rolled structures visible in the uncoated graphene oxide samples, and sonication (about 15 s to 2 min in a bath sonicator) did not produce any rolled structures.

After sonication of the coated Si wafer in 18 MΩ water (about 15 s in a bath sonicator), the resulting aqueous dispersion contained micron-sized jelly rolls. The dispersion was deposited onto a clean Si substrate for SEM observation or onto a TEM grid for TEM observation. As seen in FIGS. 2C to 2F, the jelly rolls or scrolls are about 3 microns in diameter and about tens of microns in length (about 80% between about 10-15 μm). Not to be bound by any particular theory, however, it is believed the primary role of sonication is to separate the multilayer material from the Si substrate, at which point it rolls up spontaneously. In this particular system, the Ti layer is used to enhance the adhesion between Pt and graphene oxide.

Figures 3A, 3B, 3C, 3D, 3E, 3F:
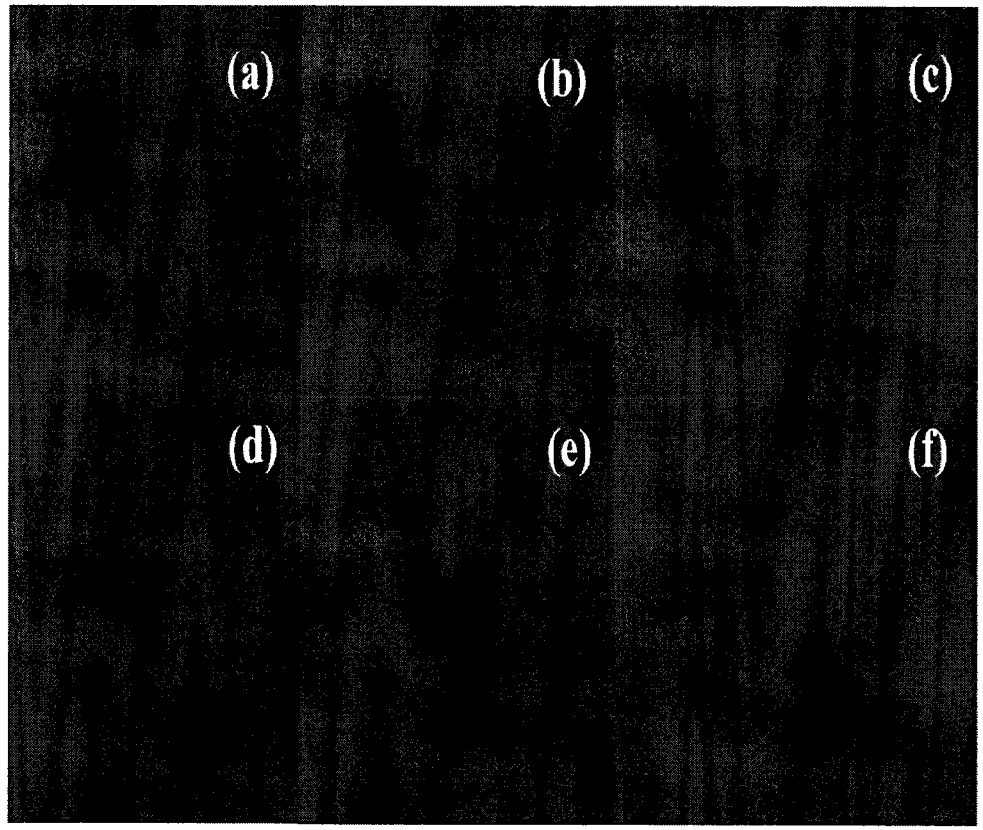
FIGS. 3A-3F are a series of static frames extracted from a video of graphene-oxide/Ti/Pt jelly rolls in motion. The total time from first to last frame is about 4 s.

Furthermore, graphene oxide/Ti/Pt jelly rolls can behave as jet engines upon introduction of about 10% aqueous hydrogen peroxide. As illustrated in FIG. 3, which contains excerpts from an optical microscopy video, the Pt-catalyzed decomposition of hydrogen peroxide creates oxygen gas microbubbles that exit from one end of the jelly roll. The expulsion of gas causes the jelly roll to move directionally rather than via Brownian motion. This behavior has been observed for tens of nanoscrolls and found that the bubbles are produced consistently at the end of the nanoscrolls, which strongly suggests that the Pt is located within the jelly roll.

REFERENCES

Kuroda, Y.; Ito, K.; Itabashi, K.; Kuroda, K. "One-Step Exfoliation of Kaolinites and Their Transformation into Nanoscrolls" *Langmuir* 2011, 27, 2028-2035.

Xie, X.; Ju, L.; Feng, X.; Sun, Y.; Zhou, R.; Liu, K.; Fan, S.; Li, Q.; Jiang, K. "Controlled Fabrication of High-Quality Carbon Nanoscrolls from Monolayer Graphene" *Nano Letters* 2009, 9, 2565-2470.

Viculis, L. M.; Mack, J. J.; Kaner, R. B. "A Chemical Route to Carbon Nanoscrolls" *Science* 2003, 299, 1361.

Yao, B. D.; Chan, Y. F.; Zhang, X. Y.; Zhang, W. F.; Yang, Z. Y.; Wang, N. "Formation mechanism of $TiO_2$ nanotubes" *App. Phys. Lett.* 2003, 82, 281-283.

Saupe, G. B.; Waraksa, C. C.; Kim, H.-N.; Han, Y. J.; Kaschak, D. M.; Skinner, D. M.; Mallouk, T. E. "Nanoscale Tubules Formed by Exfoliation of Potassium Hexaniobate" *Chem. Mater.* 2000, 12, 1556-1562.

Solovev, A. A.; Xi, W.; Gracias, D. H.; Harazim, S. M.; Deneke, C.; Sanchez, S.; Schmidt, O. G. "Self-Propelled Nanotools" *ACS Nano* 2012, DOI: 10.1021/nn204762w.

Solovev, A. A., Mei, Y., Ureña, E. B., Huang, G., Schmidt, O. G. "Catalytic Microtubular Jet Engines Self-Propelled by Accumulated Gas Bubbles" *Small* 2009, 5, 1688-1692.

Petkov, V.; Zavalij, P. Y.; Lutta, S.; Whittingham, M. S.; Parvanov, V.; Shastri, S. "Structure beyond Bragg: Study of V2O5 Nanotubes" *Phys. Rev. B* 2004, 69, 085410.

Schmidt, O. G.; Eberl, K. "Thin Solid Films Roll Up Into Nanotubes" *Nature* 2001, 410, 168.

Lipomi, D. J.; Chiechi, R. C.; Reus, W. F.; Whitesides, G. M. "Laterally Ordered Bulk Heterojunction of Conjugated Polymers: Nanoskiving a Jelly Roll" *Adv. Fund. Mater.* 2008, 18, 3469-3477.

Huang, G., Wang, J., Mei, Y. "Material considerations and locomotive capability in catalytic tubular microengines" *J. Mater. Chem.* 2012, DOI: 10.1039/c2jm16813h.

Sanchez, S.; Solovev, A. A.; Harazim, S. M.; Deneke, C.; Mei, Y. F.; Schmidt, O. G. "The Smallest Man-Made Jet Engine" *The Chemical Record* 2011, 11, 367-370.

Mirkovic, T.; Zacharia, N.; Scholes, G. D.; Ozin, G. A. "Fuel for Thought: Chemically Powered Nanomotors Out-Swim Nature's Flagellated Bacteria" *ACS Nano* 2010, 4, 1782-1787.

Bufon, C. C. B.; Gonzalez, J. D. C.; Thurmer, D. J.; Grimm, D.; Bauer, M.; Schmidt, O. G. "Self-Assembled Ultra-Compact Energy Storage Elements Based on Hybrid Nanomembranes" *Nano Letters* 2010, 10, 2506-2510.

Example 1C

Layered heterostructures containing graphene oxide (GO) nanosheets and about 20-35 nm bi-metal coatings can detach easily from a Si substrate upon sonication—spontaneously forming freestanding, micron-sized scrolls with GO on the outside—due to a combination of material stresses and weak bonding between GO layers. Simple procedures can tune the scroll diameters by varying the thicknesses of the metal films, and these results are confirmed by both experiment and modeling. The selection of materials determines the stresses that control the rolling behavior, as well as the functionality of the structures. In the GO/Ti/Pt system of the present disclosure, the Pt is located within the interior of the scrolls, which can become self-propelled microjet engines through $O_2$ bubbling when suspended in aqueous $H_2O_2$.

Recent work on controlling the three-dimensional morphology of nano- and micro-sized objects has included an increasing number of studies on scrolls. The scroll form is attractive because it is a structure with open ends and edges, adjustable interlayer distances and flexible interior volume that can be used for cargo transport. A variety of nanosheet materials can roll spontaneously into scroll structures; examples include graphene,[1,2] vanadium oxide,[3] potassium niobate,[4,5] titania,[6] lead oxide,[7] nickel,[8] and kaolinite.[9] In particular, carbon-based nanoscrolls, which are expected to have future applications as actuators, hydrogen storage materials, and drug delivery platforms,[10-12] have been produced by methods ranging from chemical intercalation in graphite,[1,2] microexplosion,[13] microwave spark assistance,[14] and surface strain engineering.[15]

In addition, several nanostructured heterolayer systems are known to exhibit scrolling behavior. Major efforts have involved metal and metal oxide (especially semiconductor) multilayers deposited on a sacrificial material layer.[16-18] Upon etching (removing the sacrificial layer), the released heterostructures spontaneously roll into micron-sized scrolls/tubes, which can be described evocatively as "jelly rolls".[19] For example, InAs/GaAs nanotubes and nanohelices,[20] $In_xGa_{1-x}As/GaAs$ rectangular membranes and scrolls,[21,22] and multilayer Pt/Au/Fe/Ti microtubes[23] have been produced using this approach.

The present disclosure describes multilayered heterostructures that contain graphene oxide (GO) nanosheets and exhibit spontaneous rolling behavior. The functions of the GO are to act as a support for the metallic multilayer and to provide an easily cleavable interface between the substrate and the vapor deposited metal layers, which allows the heterostructures to detach from the surface and roll into free-standing scrolls. This design strategy has not been applied to self-rolling nanostructured scrolls, despite the advantages: the fact that it extends the range of material components in such structures, and it is experimentally convenient (because it eliminates the need for an etching step, uses an aqueous dispersion of GO, and does not require epitaxially-grown or lithographically-defined starting materials).

Figures 5A, 5B, 5C, 5D, 5E:
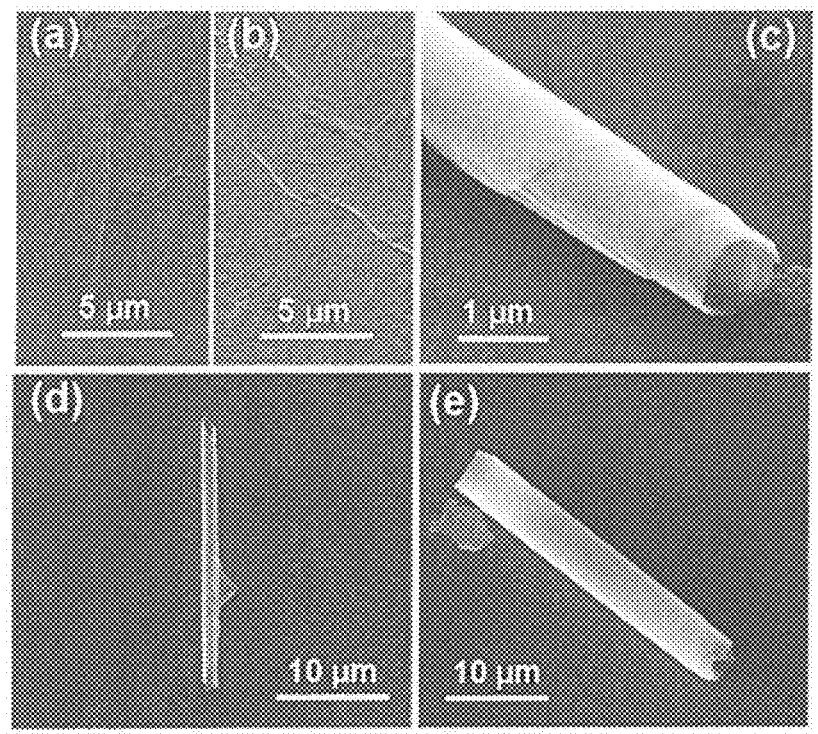
FIGS. 5A-5E illustrate representative SEM images: (a) GO on Si substrate before Ti/Pt coating. (b) GO on Si substrate after Ti/Pt coating. (c) A typical GO/Ti/Pt scroll with 10 nm Ti and 10 nm Pt from a tilt view. Images (d) and (e) show typical GO/Ti/Pt scrolls with 10 nm Ti/10 nm Pt and 10 nm Ti/25 nm Pt.

An embodiment of the present disclosure includes GO, titanium, and platinum (GO/Ti/Pt). To fabricate this multi-layed structure, an aqueous dispersion of GO nanosheets was drop-cast on a silicon wafer, and then electron-beam evaporation was used to coat the GO with titanium (about 10 nm) followed by platinum (about 10 nm). Scanning electron microscopy (SEM) images before and after coating (FIGS. 5A-5B) show that there are no scrolled structures at these points, only wrinkles originating in the GO layer.

Figures 6A, 6B:
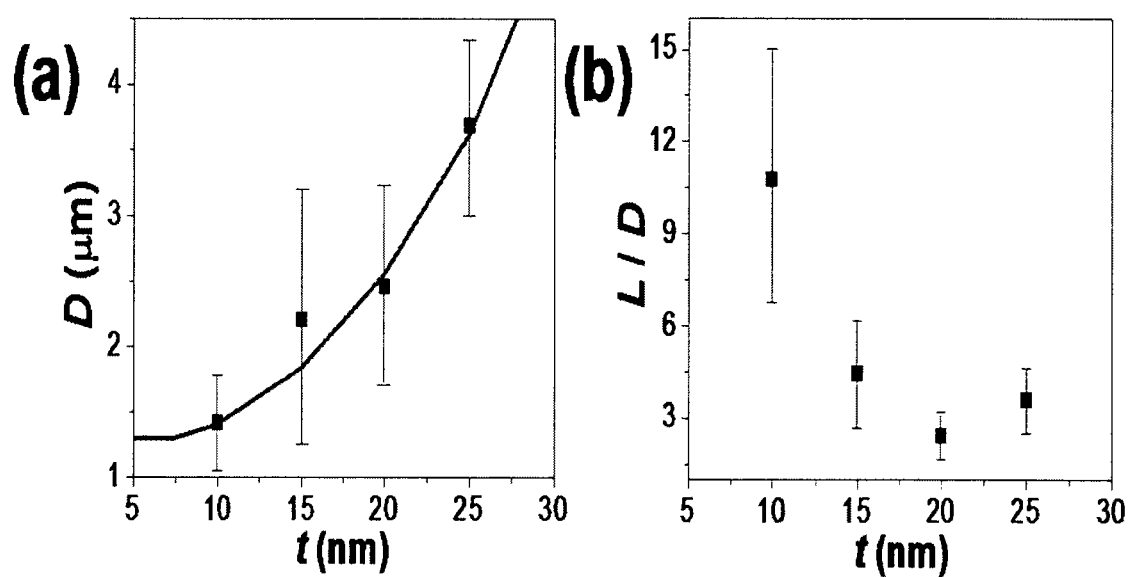
FIGS. 6A-6B are graphs that illustrate (a) Average scroll diameter D as a function of Pt thickness t and the best fit (curve) using a stressed composite plate theory. (b) A plot of the scroll aspect ratio L/D versus the Pt thickness t.
Figures 10A, 10B:
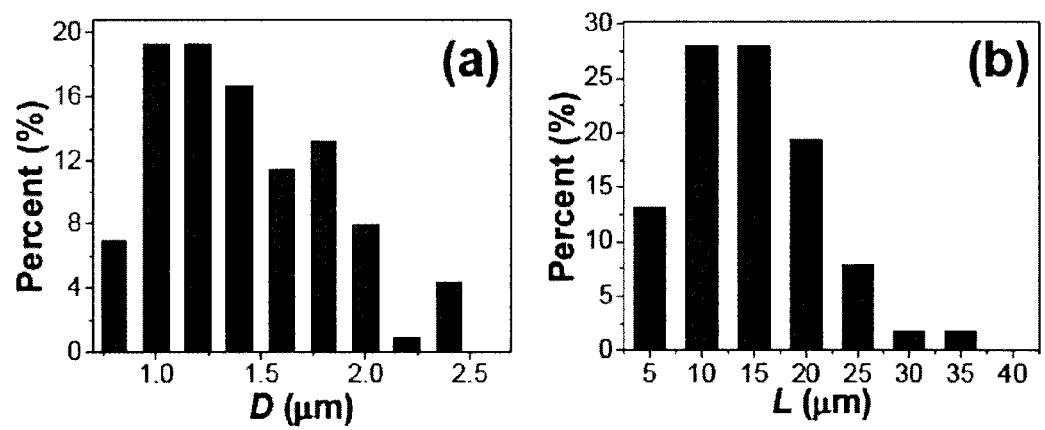
FIGS. 10A-10B are graphs that illustrate (a) diameter (D) and (b) length (L) distribution of 114 GO/Ti/Pt scrolls. The average diameter=1.4+/−0.4 μm and the average length=14.9+/−6.6 μm.
Figures 11A, 11B:
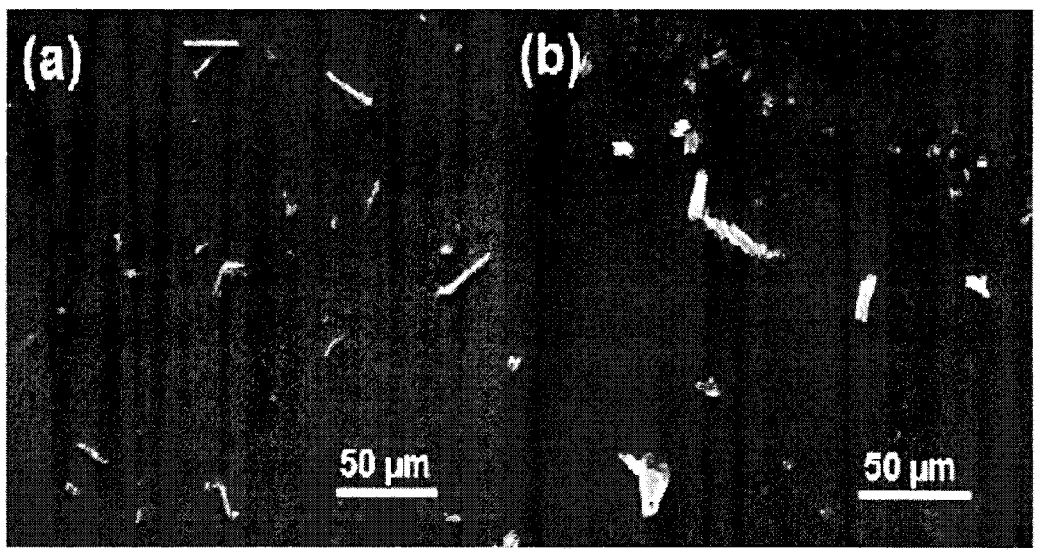
FIGS. 11A-11B are SEM images showing large areas with many scrolls for comparison. (a) Scrolls with about 10 nm Ti and about 10 nm Pt. (b) Scrolls with about 10 nm Ti and about 25 nm Pt.
Figures 12A, 12B, 12C, 12D, 12E, 12F:
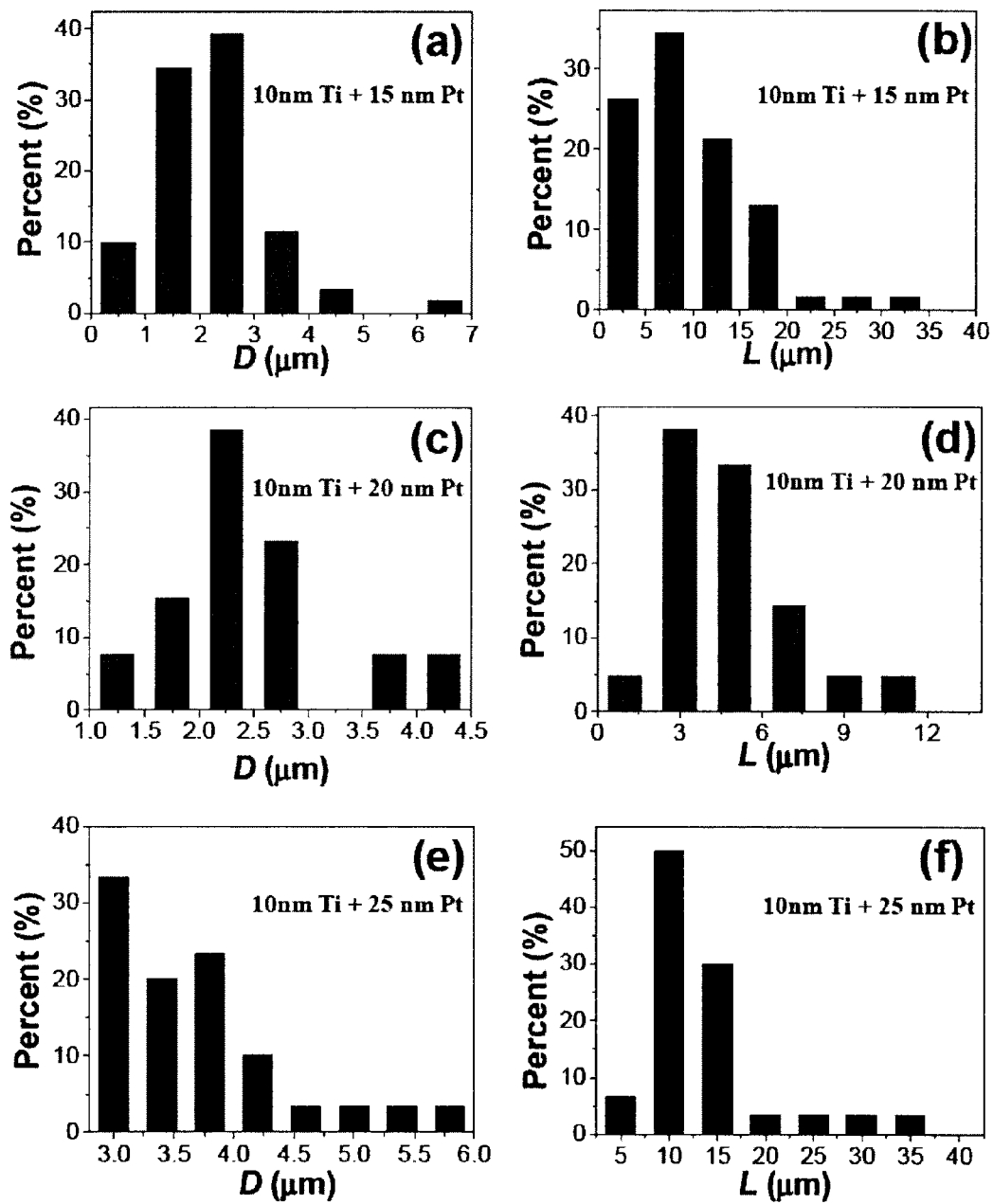
FIGS. 12A-12F are graphs that illustrate size distribution of GO/Ti/Pt scrolls incorporating Pt films with different thicknesses (about 15-25 nm).
Figure 13:
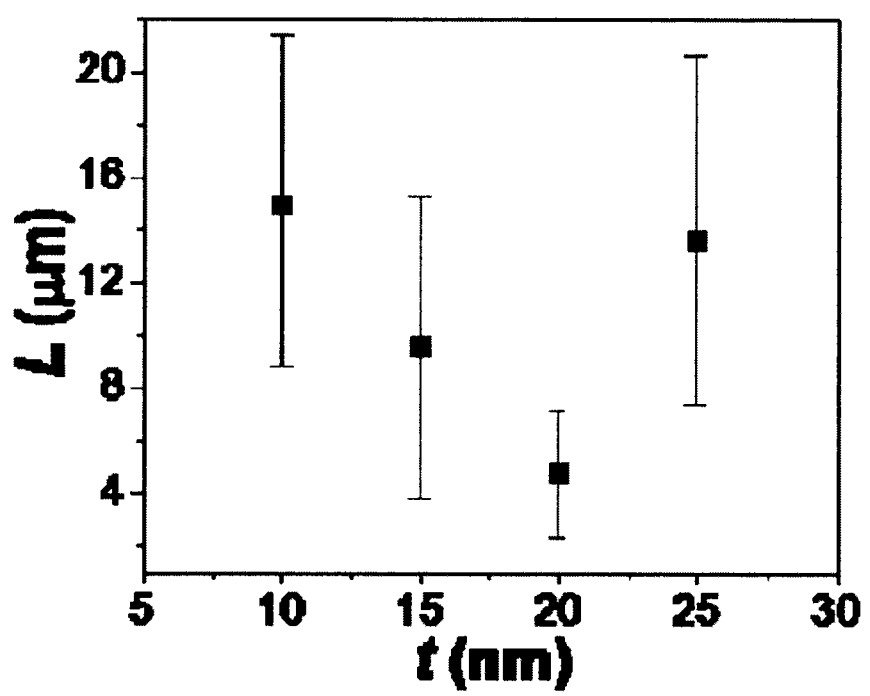
FIG. 13 illustrates scroll length (L) with respect to Pt thickness.
Figures 14A, 14B:
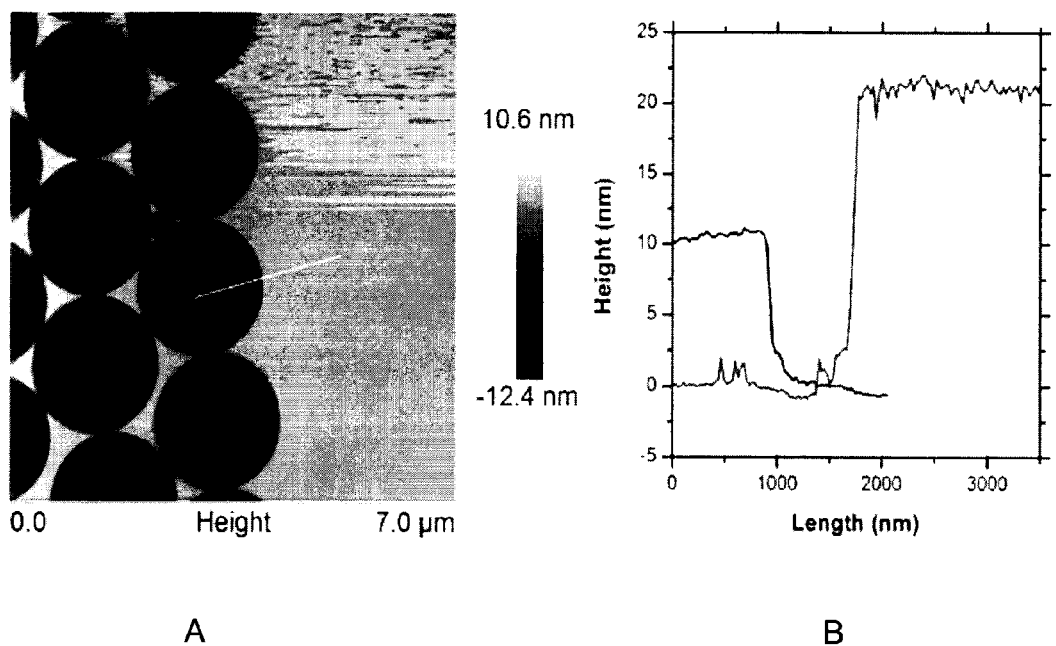
FIGS. 14A-14B illustrate a topographical AFM image of the Ti/Pt film and the exposed Si substrate as well as graphed step heights showing the measured thickness from layers of Ti (short curve) and Ti+Pt (long curve).
Figure 15A:
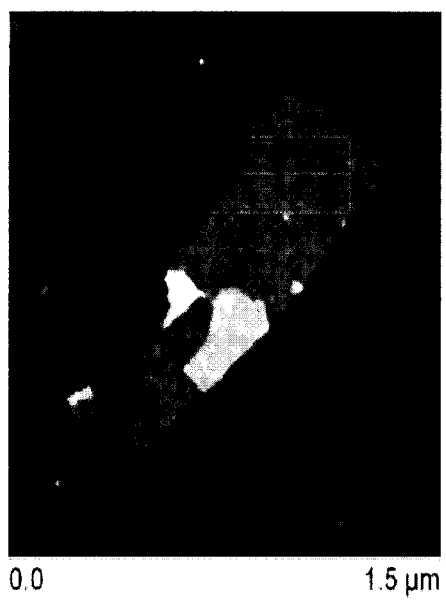
FIGS. 15A-15B illustrate a topographical AFM tapping mode image of a GO nanosheet after annealing, with a graphical representation depicting the mean step height from substrate to nanosheet.
Figure 15B:
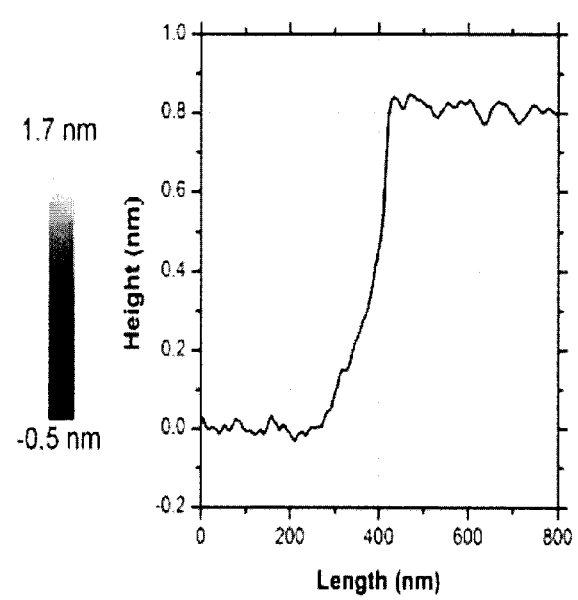
Figure 16:
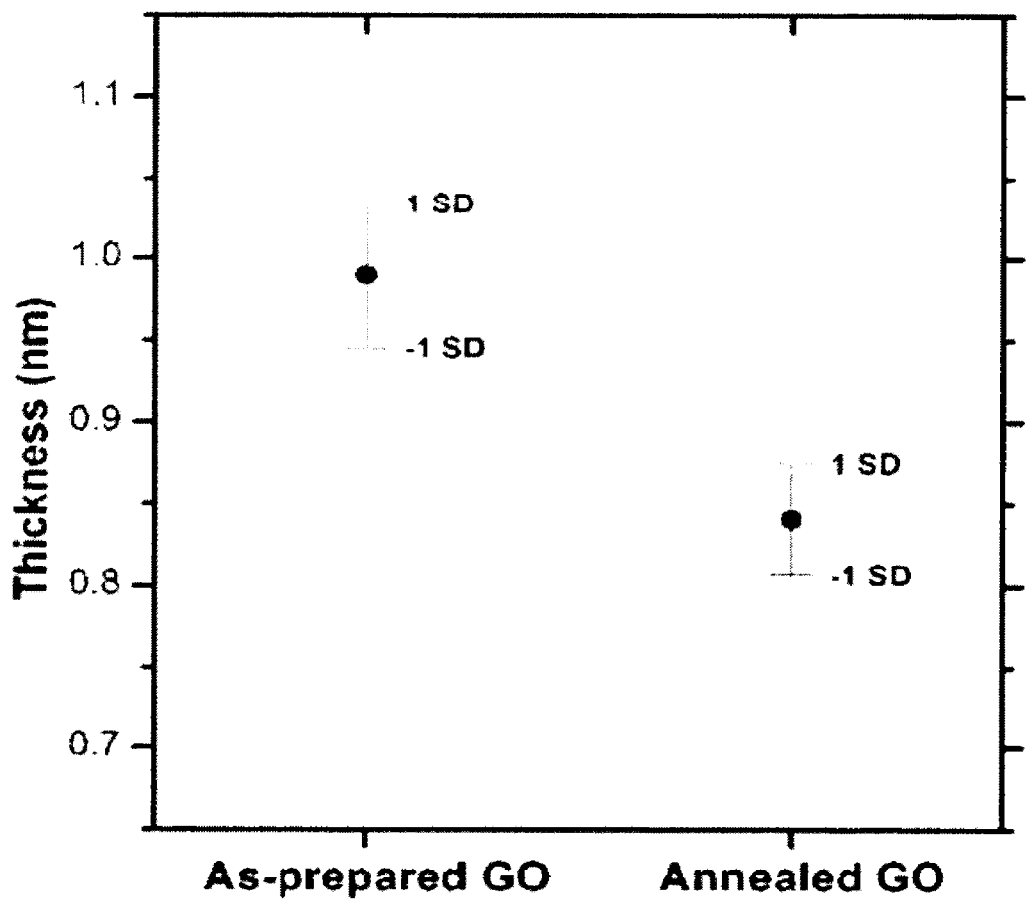
FIG. 16 illustrates size distribution of nanosheets from as-prepared GO and annealed GO samples. The black spots indicate the calculated mean thickness for each set of nanosheets.

Upon sonication of the GO/Ti/Pt-coated wafer in water, the multilayer film fragments into multi-micron-sized pieces that detach from the surface and spontaneously roll into full or partial scrolls (FIGS. 5B-C and FIGS. 9A-9D). A size distribution analysis of more than 100 scrolls reveals that their diameters are typically about 1-2 μm (average diameter: 1.4±0.4 μm) and their lengths are about 10-20 μm (average length: 15±7 μm) (FIGS. 10A-10B). Furthermore, the diameters of the scrolls have been tuned by varying the thickness of the platinum layer from about 10 to 25 nm (FIGS. 11A-11B and FIGS. 12A-12F). For example, FIG. 5E shows an SEM image of a typical scroll containing about 10 nm Ti and about 25 nm Pt. The average diameters of such scrolls are larger than that of scrolls with about 10 nm Pt. In fact, the average scroll diameter (D) as a function of Pt thickness (t) plotted in FIG. 6A shows a monotonic increase of D with t. No obvious dependence of average scroll length (L) on t was observed (FIG. 13). This is expected because the size distribution and shape of GO nanosheets in all experiments are statistically the same, and these parameters should determine the length of the scrolls.[24] Thus, the calculated scroll aspect ratio (L/D) versus t shows a decreasing trend (FIG. 6B).

Figure 7:
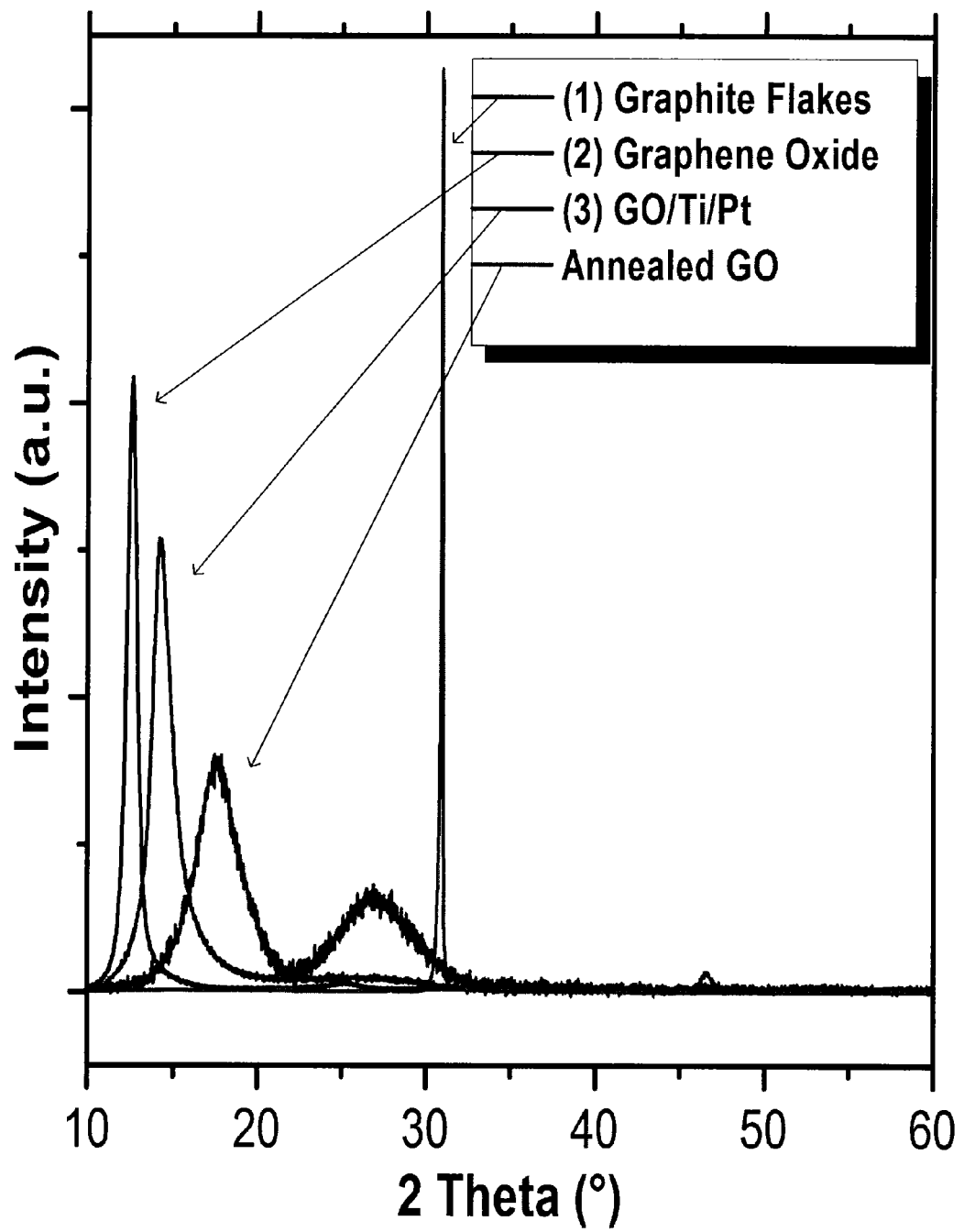
FIG. 7 is a graph that illustrates XRD data collected from graphite flakes (starting material for GO), exfoliated GO nanosheets on Si, GO/Ti/Pt layers on Si, and annealed (120° C.) GO nanosheets on Si.
Figures 17A, 17B:
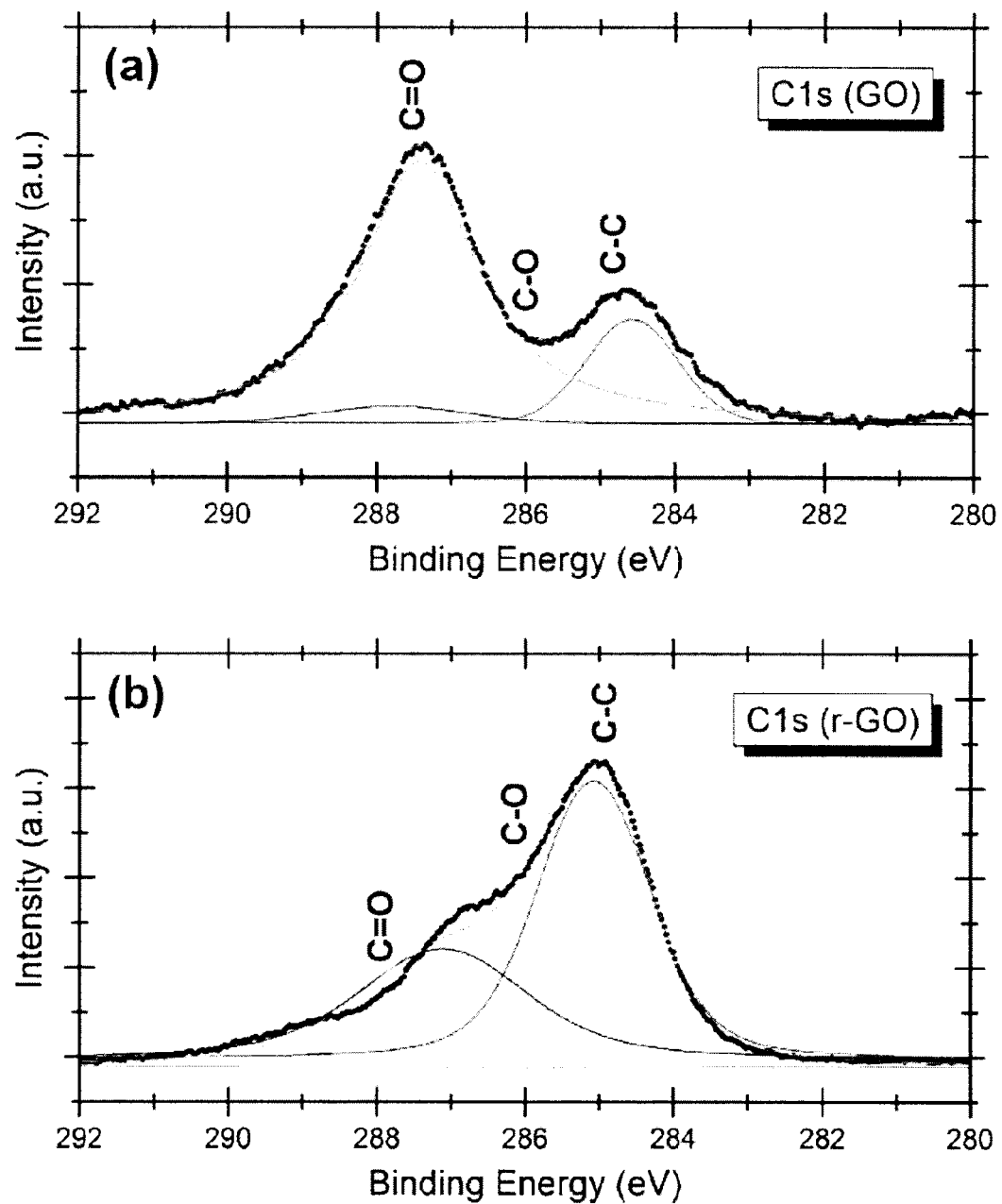
FIGS. 17A-17B are graphs that illustrate XPS data for the C 1s orbital of GO sheets before (a) and after (b) metal deposition.
Figure 18A:
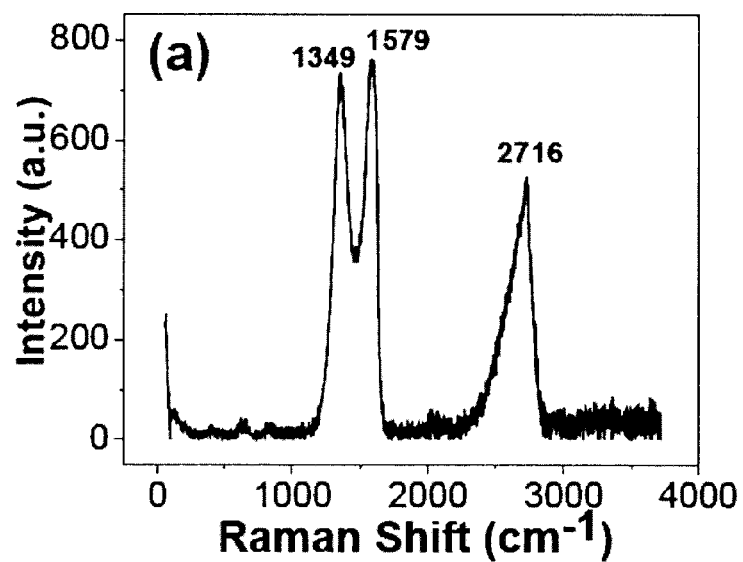
FIGS. 18A-18B are graphs that illustrate (a) Raman spectrum of a layered sample of as-prepared GO nanosheets. (b) Comparison of D and G bands from GO before (GO) and after (r-GO) metal deposition.
Figure 18B:
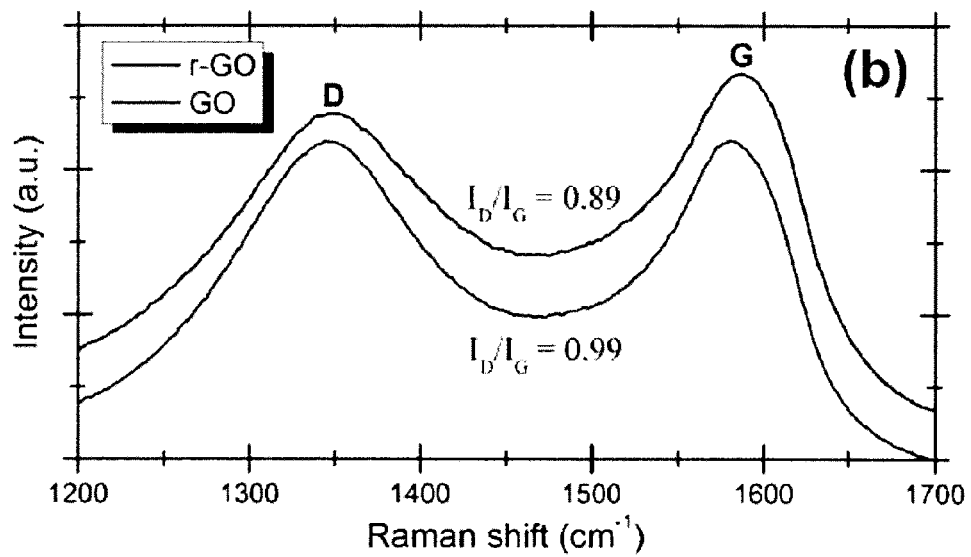

GO bilayers in the scrolls relate to the interaction between GO and the metal coatings. In fact, further characterizations using X-ray diffraction (XRD), X-ray photoelectron spectroscopy (XPS), and Raman spectroscopy all indicate that the nature of the GO changes after metal deposition. For example, FIG. 7 shows the changing XRD patterns collected along the fabrication process, from (1) graphite starting material to (2) as-prepared GO nanosheets to (3) GO/Ti/Pt multilayers (not yet scrolled). The XRD pattern of the GO nanosheets exhibits a characteristic (002) peak at 12.5° (GO curve), which can be correlated to an interlayer spacing of about 0.807 nm. For comparison, the original graphite flakes exhibit a sharp peak at 31° (graphite flakes curve), corresponding to an interlayer spacing of about 0.335 nm. This change in basal plane d-spacing is typical for graphite vs. GO.[31] However, after metal deposition, the (002) peak of GO clearly shifts to 15°, consistent with GO reduction. In this sample, the Pt (111) peak at 46° (GO/Ti/Pt curve) also is visible. To corroborate GO reduction, GO nanosheets on Si were heated to about 120° C. for about 24 hours. This annealing process resulted in a diffraction pattern typically exhibited by partially reduced GO, characterized by broad peaks shifted to higher angles of 2θ, 17.5° and 26° (annealed GO curve in FIG. 7).[32] Additional data from XPS and Raman spectroscopy further support a GO reduction mechanism. To summarize, XPS shows a shift in relative intensity from C=O to C—C bonding after metal deposition (FIG. 17), consistent with the observation by Ajayan and co-workers,[33] and Raman spectroscopy indicates enhanced localized $sp^3$ defects, which is characteristic of reduction (FIG. 18). It is concluded that metal deposition has a mild reducing effect on the GO nanosheets, causing the loss of predominantly carbonyl-containing functional groups and dissociation of water molecules.[32] Thus, the GO in GO/Ti/Pt appears to be intermediate in chemical and crystallographic character between as-prepared GO and fully reduced GO. Such a reduction effect should have two consequences: first, it suggests that the Ti layer interacts strongly with the adjacent GO, which leads to strong adhesion between the Ti and contacted GO monolayer; second, the reduction is a local effect confined to only the Ti-GO interface and immediately adjacent GO layers. Thus, the Ti acts as "glue" to attach approximately two GO monolayers and the Pt layer tightly within this layered structure.

In the GO/Ti/Pt structure, each material layer contributes to the overall scrolling behavior. The highly anisotropic dimensions of GO nanosheets (nm×microns×microns) cause them to assemble in parallel stacked arrangements within concentrated dispersions or dried forms.[34] The titanium layer enhances the adhesion between GO and Pt, and it induces GO reduction within approximately the first two contacted monolayers. These effects make the bilayer GO/Ti/Pt a tightly-bonded three component system. The residue stresses from the Ti and Pt layers cause this heterostructure to curl due to the relatively weak van der Waals interactions between GO nanosheet layers, which then allows the facile separation of the heterostructure from the substrate and further curling into scrolls. We emphasize that the detachment mechanism in this system is a physical delamination process, where the cleavage plane is within the top few nanometers of a much thicker GO film. Through this process, approximately two monolayers of partially reduced GO are incorporated on the outer surface of the scroll while excess GO remains on the substrate. The additional residue stress introduced by the Pt layer can tune the scroll diameter, and this material also can provide catalytic activity.

Figures 8A, 8B, 8C:
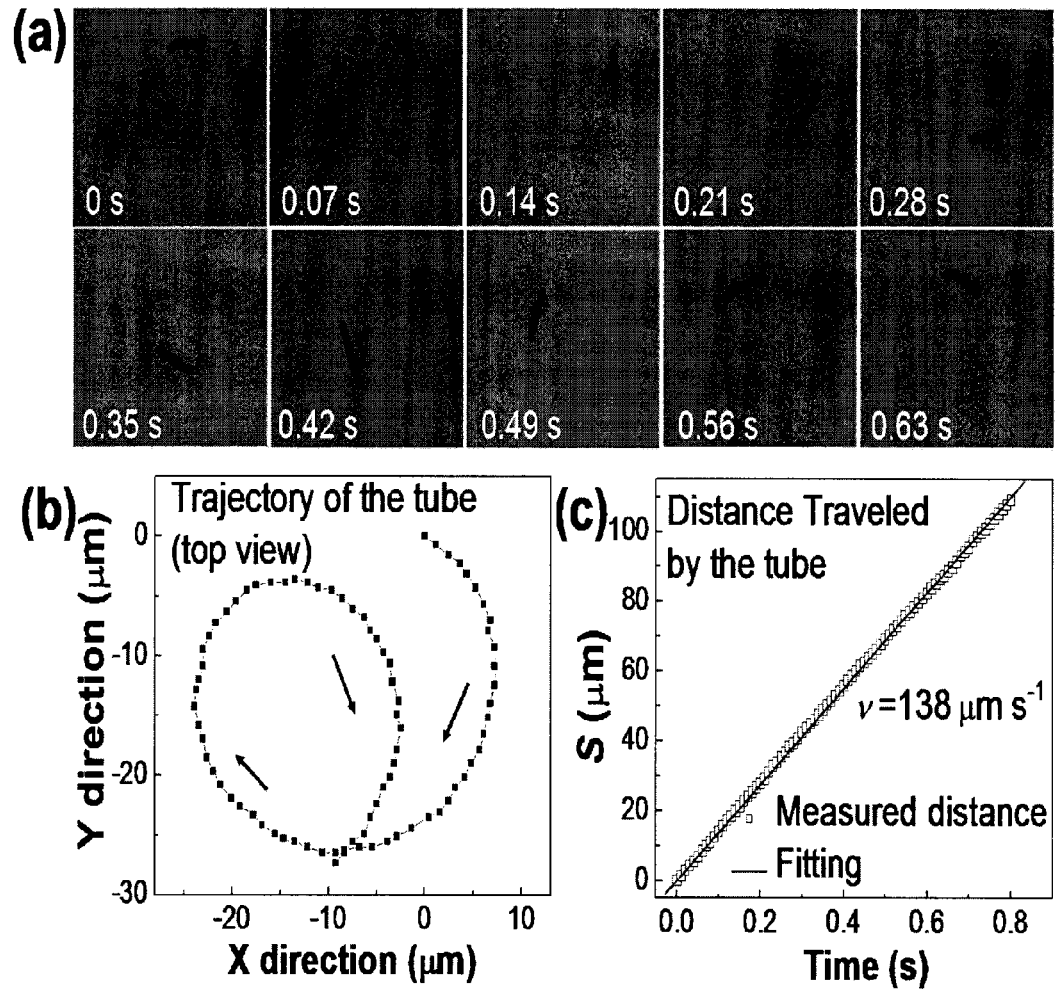
FIGS. 8A-8C illustrate (a) A series of static frames extracted from the video of a GO/Ti/Pt scroll in motion in aqueous $H_2O_2$. (b) Top view of the trajectory of this scroll in the X-Y plane. (c) A plot of distance with respect to time calculated from (b) and the linear fit.
Figure 9A:
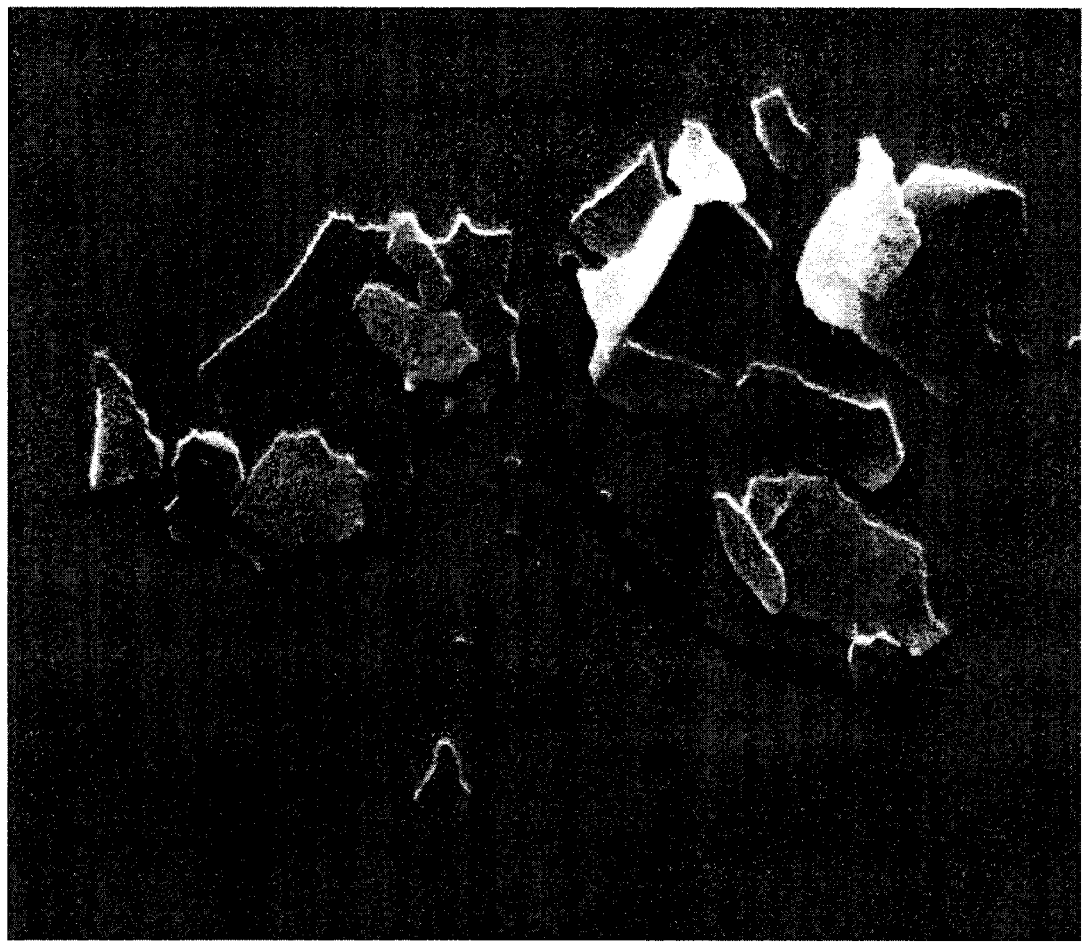
FIGS. 9A-9D are SEM images of small pieces of GO/Ti/Pt heterostructure and some partially rolled structures.
Figure 9B:
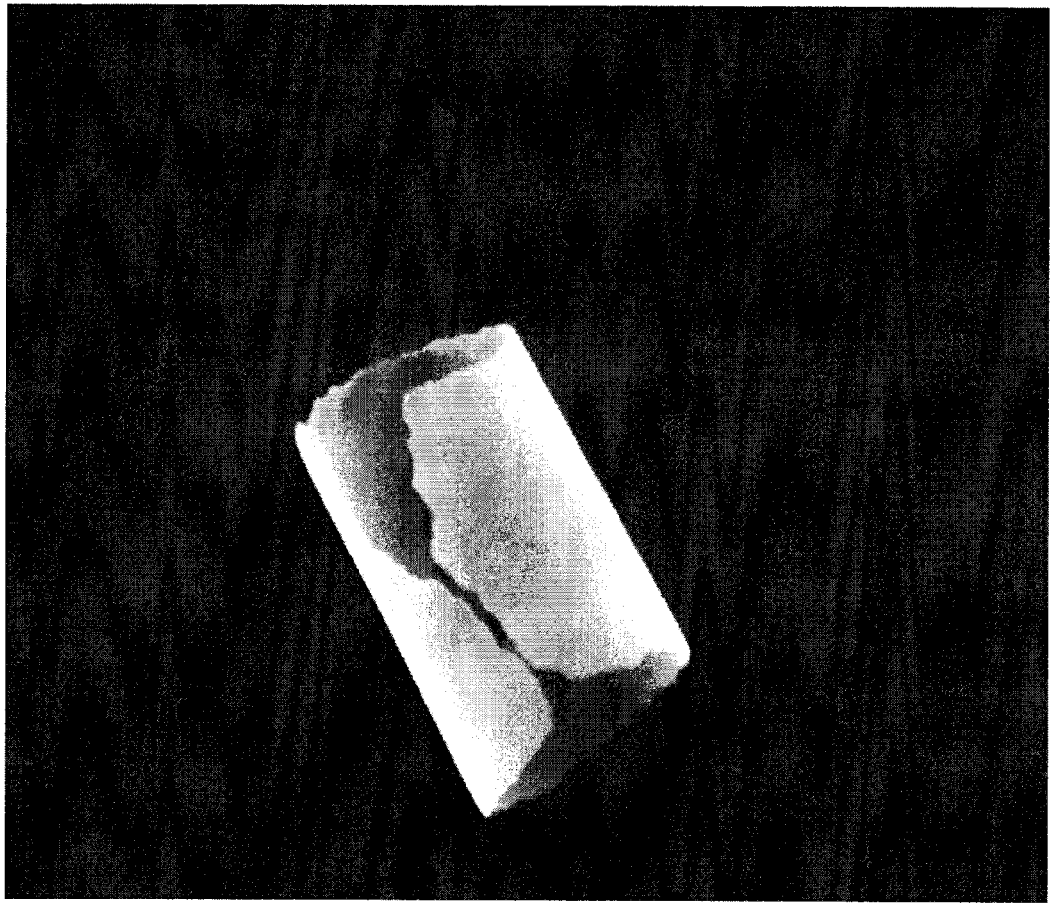
Figure 9C:
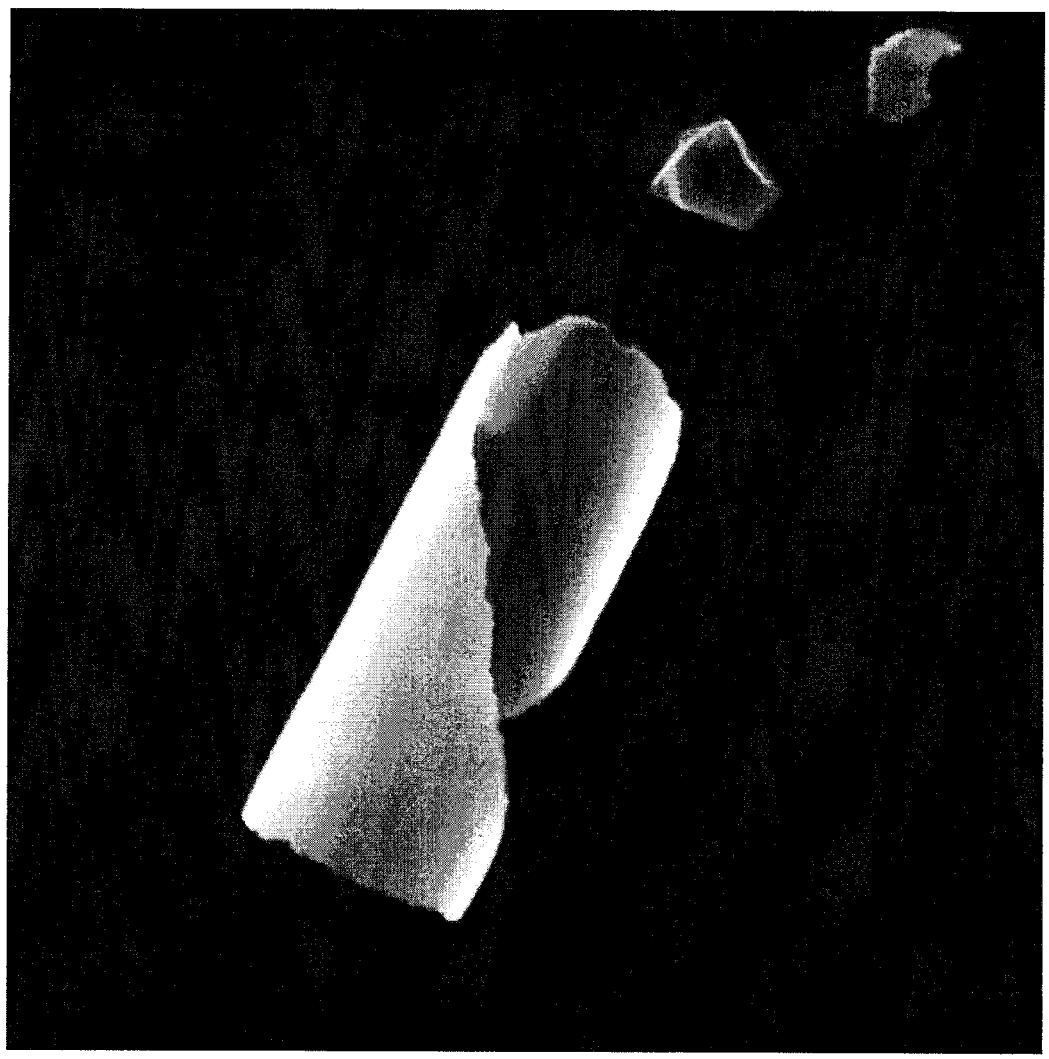
Figure 9D:
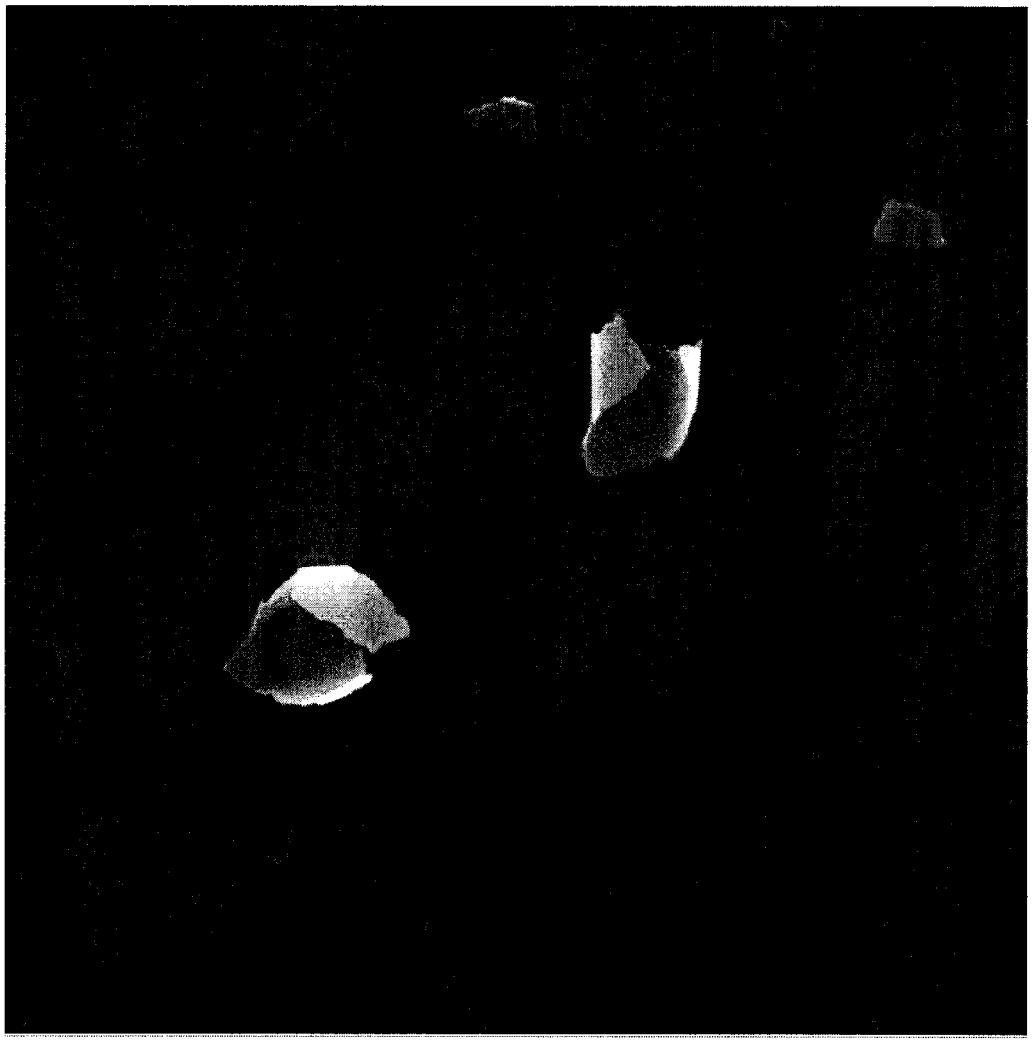

A stress model predicts that the Pt layer is wrapped inside the scroll, and thus such a structure can act as a "microjet engine" in the presence of $H_2O_2$, which reacts with the platinum catalyst to create $O_2$.[23,35,36] Gas bubbles of $O_2$ generated by the reaction typically exit from one end of the scroll and drive it to move directionally in the liquid. FIG. 8A shows representative movie frames extracted from a video (50× magnification objective lens). An analysis of the trajectory of this scroll in the horizontal plane reveals circular/spiral type motion (FIG. 8B). By examining the total traveling distance $$S\left(\equiv \sum_{i=2}^{n} \sqrt{(x_i - x_{i-1})^2 + (y_i - y_{i-1})^2}\right)$$

versus time, as shown in FIG. 8C, it is further shown that the scroll moves at a nearly constant speed (v) of about 138 μm s$^{-1}$, which is about twelve body-lengths s$^{-1}$. This speed is comparable to flagellated bacteria, which are some of the fastest organisms on Earth.[37] In fact, even greater speeds (up to 200 to 350 body-lengths s$^{-1}$) have been reported for scroll microjets in previous studies.[37,38]

Figures 19A, 19B, 19C:
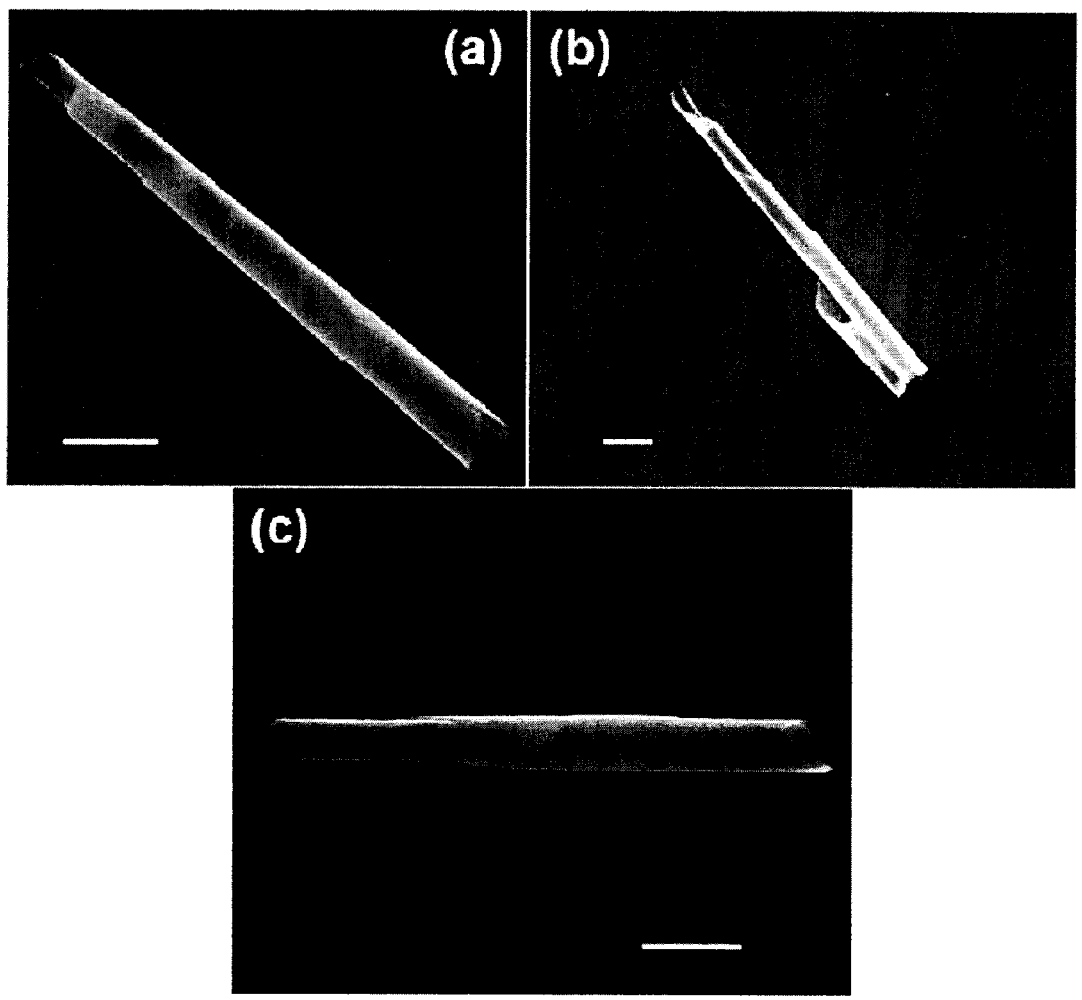
FIGS. 19A-19C are SEM images of scrolls with about 10 nm Ti and about 10 nm Pt that highlight the asymmetry of the scrolls. All the scale bars are 2 µm.

The motions of tens of scrolls have been examined and it was found that all exhibit similar circular/spiral motion. However, speed and direction depend on many factors, such as the frequency and maximum size of the bubbles generated, the exact location of the bubbles with respect to the central axis of the scroll, and whether the bubbles leave the scroll (eject) or burst without ejecting. Although the bubbles usually were ejected from one end of a scroll, we observed bubbles emerging from both ends in a few cases. It is likely that bubbles often appear at only one end because of the asymmetric, slightly conical geometry of most scrolls (see FIG. 5 and FIG. 19); when the diameter of one end of the scroll is slightly larger than the other, the bubbles emerge from the end with the larger diameter. Other parameters, such as the shape of the scroll end and spontaneous fluctuation (symmetry broken due to noise), also could induce such a phenomenon. Nevertheless, bubbles were generated consistently from the ends, confirming that the platinum layer is located inside the scrolls. It is believed that both the circular/spiral motion and the differences in bubble production are caused by small inhomogeneities in the layers and variations in the nature of the scrolling.

In summary, the present disclosure includes a facile method to fabricate multilayered, freestanding nanostructured scrolls, in which each material has been tailored to make both structural and functional contributions. In particular, the GO layer makes a maximum contribution with a minimal thickness that is consistent with miniaturization efforts.

Experimental Section

Deposition of the Multilayered Heterostructure and Rolling-Up:

An aqueous dispersion of GO nanosheets was drop-cast onto clean 1×1 cm$^2$ silicon substrates. These substrates were placed on a hot plate and dried in air at about 100° C. for about ten minutes, and then loaded into the evaporation system (Torr International, New Windsor, N.Y.) for electron-beam evaporation in a vacuum environment (10$^{-6}$ Torr) at a vapor incidence angle of 0°. Both Ti and Pt were deposited at a rate of about 0.2 Å s$^{-1}$, read by a quartz crystal microbalance (QCM) facing directly toward the incident vapor. Next, the substrates coated with multilayer film were immersed in an 18 MΩ aqueous solution, and fragmented into multi-micron-sized pieces and spontaneously scrolled into scrolls during a sonication (less than about 1 minute).

Jet Engine Activity:

about 5 μL of an aqueous dispersion containing the scrolls were pipetted onto a clean Si substrate, followed by the introduction of about 5 μL of 10% $H_2O_2$ to activate the motion. After a steady reaction rate was reached and observed (about one minute), pictures and videos of jet engine motion were captured by a Mitituya FS110 optical microscope with an Imperx charge-coupled device (CCD) camera (Phantom v9.1) mounted onto the trinocular head, using 10× and 50× magnification objective lens.

REFERENCES (1) Viculis, L. M.; Mack, J. J.; Kaner, R. B. A Chemical Route to Carbon Nanoscrolls. *Science* 2003, 299, 1361-1361.
(2) Shioyama, T. A. H. A New Route to Carbon Nanotubes. *Carbon* 2003, 41, 179-198.
(3) Muhr, H.-J.; Krumeich, F.; Schönholzer, U. P.; Bieri, F.; Niederberger, M.; Gauckler, L. J.; Nesper, R. Vanadium Oxide Nanotubes—A New Flexible Vanadate Nanophase. *Adv. Mater.* 2000, 12, 231-234.
(4) Saupe, G. B.; Waraksa, C. C.; Kim, H.-N.; Han, Y. J.; Kaschak, D. M.; Skinner, D. M.; Mallouk, T. E. Nanoscale Tubules Formed by Exfoliation of Potassium Hexaniobate. *Chem. Mater.* 2000, 12, 1556-1562.
(5) Ma, R.; Sasaki, T. Chapter 10: Inorganic and Metallic Nanotubular Materials in *Topics in Applied Physics* 2010, 117, 135-146.
(6) Yao, B. D.; Chan, J. F.; Zhang, X. Y.; Zhang, W. F.; Yang, Z. Y.; Wang, N. Formation Mechanism of $TiO_2$ Nanotubes. *App. Phys. Lett.* 2003, 82, 281-283.
(7) Shi, L.; Xu, Y.; Li, Q. Controlled Growth of Lead Oxide Nanosheets, Scrolled Nanotubes, and Nanorods. *Cryst. Growth & Design* 2008, 8, 3521-3525.
(8) Zhang, G.; Sun, S.; Li, R.; Zhang, Y.; Cai, M.; Sun, X. Large-Scale Aqueous Synthesis and Growth Mechanism of Single-Crystalline Metal Nanoscrolls at Room Temperature: The Case of Nickel. *Chem. Mater.* 2010, 22, 4721-4727.
(9) Kuroda, Y.; Ito, K.; Itabashi, K.; Kuroda, K. One-Step Exfoliation of Kaolinites and Their Transformation into Nanoscrolls. *Langmuir* 2011, 27, 2028-2035.
(10) Braga, S. F.; Coluci, V. R.; Legoas, S. B.; Giro, R.; Galvão, D. S.; Baughman, R. H. Structure and Dynamics of Carbon Nanoscrolls. *Nano Lett.* 2004, 4, 881-884.
(11) Mpourmpakis, G.; Tylianakis, E.; Froudakis, G. E. Carbon Nanoscrolls: A Promising Material for Hydrogen Storage. *Nano Lett.* 2007, 7, 1893-1897.
(12) Shi, X.; Pugno, N. M.; Gao, H. Tunable Core Size of Carbon Nanoscrolls. *J. Comput. Theor. Nanos.* 2010, 7, 517-521.
(13) Zeng, F.; Kuang, Y.; Wang, Y.; Huang, Z.; Fu, C.; Zhou, H. Facile Preparation of High-Quality Graphene Scrolls from Graphite Oxide by a Microexplosion Method. *Adv. Mater.* 2011, 23, 4929-4932.
(14) Zheng, J.; Liu, H.; Wu, B.; Guo, Y.; Wu, T.; Yu, G.; Liu, Y.; Zhu, D. Production of High-Quality Carbon Nanoscrolls with Microwave Spark Assistance in Liquid Nitrogen. *Adv. Mater.* 2011, 23, 2460-2463.

(15) Xie, X.; Ju, L.; Feng, X.; Sun, Y.; Zhou, R.; Liu, K.; Fan, S.; Li, Q.; Jiang, K. Controlled Fabrication of High-Quality Carbon Nanoscrolls from Monolayer Graphene. *Nano Lett.* 2009, 9, 2565-2570.

(16) Rogers, J. A.; Lagally, M. G.; Nuzzo, R. G. Synthesis, Assembly and Applications of Semiconductor Nanomembranes. *Nature* 2011, 477, 45-53.

(17) Huang, G.; Mei, Y. Thinning and Shaping Solid Films into Functional and Integrative Nanomembranes. *Adv. Mater.* 2012, 24, 2517-2546.

(18) Li, X. Strain Induced Semiconductor Nanotubes: from Formation Process to Device Applications. *J. Phys. D.: Appl. Phys.* 2008, 41, 193001.

(19) Lipomi, D. J.; Chiechi, R. C.; Reus, W. F.; Whitesides, G. M. Laterally Ordered Bulk Heterojunction of Conjugated Polymers: Nanoskiving a Jelly Roll. *Adv. Funct. Mater.* 2008, 18, 3469-3477.

(20) Prinz, V. Y.; Seleznev, V. A.; Gutakovsky, A. K.; Chehovskiy, A. V.; Preobrazhenskii, V. V.; Putyato, M. A.; Gavrilova, T. A. Free-Standing and Overgrown InGaAs/GaAs Nanotubes, Nanohelices and Their Arrays. *Physica E,* 2000, 6, 828-831.

(21) Chun, I. S.; Challa, A.; Derickson, B.; Hsia, K. J.; Li, X. Geometry Effect on the Strain-Induced Self-Rolling of Semiconductor Membranes. *Nano Lett.* 2010, 10, 3927-3932.

(22) Schumacher, O.; Mendach, S.; Welsch, H.; Schramm, A.; Heyn, C.; Hansen, W. Lithographically Defined Metal-Semiconductor-Hybrid Nanoscrolls. *App. Phys. Lett.* 2005, 86, 143109.

(23) Solovev, A. A.; Mei, Y.; Bermúdez Ureña, E.; Huang, G.; Schmidt, O. G. Catalytic Microtubular Jet Engines Self-Propelled by Accumulated Gas Bubbles. *Small,* 2009, 5, 1688-1692.

(24) Stoychev, G.; Zakharchenko, S.; Turcaud, S.; Dunlop, J. W. C.; Ionov, L. Shape-Programmed Folding of Stimuli-Responsive Polymer Bilayers. *ACS Nano* 2012, 6, 3925-3934.

(25) Timoshenko, S.; Woinowsky-Krieger, S. *Theory of Plates and Shells,* McGraw-Hill Book Company, NY, 1959.

(26) Beer, F. P.; Johnston, E. R.; DeWolf, J. T. *Mechanics of Materials,* McGraw-Hill Higher Education, 2006.

(27) Suk, J. W.; Piner, R. D.; An, J.; Ruoff, R. S. Mechanical Properties of Monolayer Graphene Oxide. *ACS Nano* 2010, 4, 6557-6564.

(28) Tsuchiya, T.; Hirata, M.; Chiba, N. Young's Modulus, Fracture Strain, and Tensile Strength of Sputtered Titanium Thin Films. *Thin Solid Films* 2005, 484, 245-250.

(29) Salvadori, M.; Brown, I.; Vaz, A.; Melo, L.; Cattani, M. Measurement of the Elastic Modulus of Nanostructured Gold and Platinum Thin Films. *Phys. Rev. B* 2003, 67, 153404.

(30) Ivill, M.; Cole, M. W.; Hirsch, S. G.; Hubbard, C. Residual Stress of Pt Films with Ti and $TiO_x$ Adhesion Layers on Si and Sapphire Substrates. *Integr. Ferroelectr,* 2010, 111, 37-49.

(31) Dubin, S.; Gilje, S.; Wang, K.; Tung, V. C.; Cha, K.; Hall, A. S.; Farrar, J.; Varshneya, R.; Yang, Y.; Kaner, R. B. A One-Step, Solvothermal Reduction Method for Producing Reduced Graphene Oxide Dispersions in Organic Solvents. *ACS Nano* 2010, 4, 3845-3852.

(32) Huh, S. H. Chapter 5: Thermal Reduction of Graphene Oxide in *Physics and Applications of Graphene—Experiments,* Ed: S. Mikhailov, InTech, 2011.

(33) Mathkar, A.; Tozier, D.; Cox, P.; Ong, P.; Galande, C.; Balakrishnan, K.; Reddy, A. L. M.; Ajayan, P. M. Controlled, Stepwise Reduction and Band Gap Manipulation of Graphene Oxide, *J. Phys. Chem. Lett.* 2012, 3, 986-991.

(34) Kim, J. E.; Han, T. H.; Lee, S. H.; Kim, J. Y.; Ahn, C. W.; Yun, J. M.; Kim, S. O. Graphene Oxide Liquid Crystals. *Angew. Chem. Int. Ed.,* 2011, 50, 3043-3047.

(35) Gibbs, J. G.; Kothari, S.; Saintillan, D.; Zhao, Y. P. Geometrically Designing the Kinematic Behavior of Catalytic Nanomotors. *Nano Lett.* 2011, 11, 2543-2550.

(36) Fournier-Bidoz, S. B.; Arsenault, A. C.; Manners, I.; Ozin, G. A., Synthetic Self-Propelled Nanorotors. *Chem. Commun.* 2005, 41, 441-443.

(37) Sanchez, S.; Solovev, A. A.; Harazim, S. M.; Schmidt, O. G. Microbots Swimming in the Flowing Streams of Microfluidic Channels. *J. Am. Chem. Soc.* 2011, 133, 701-703.

(38) Gao, W.; Sattayasamitsathit, S.; Orozco, J.; Wang, J. Highly Efficient Catalytic Microengines: Template Electrosynthesis of Polyaniline/Platinum Microtubes. *J. Am. Chem. Soc.* 2011, 133, 11862-11864.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In an embodiment, the term "about" can include traditional rounding according to measurement techniques and the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of the disclosure. Many variations and modifications may be made to the above-described embodiments. All such modifications and variations are intended to be included herein within the scope of this disclosure and protected by the following claims.

Therefore, at least the following is claimed:

1. A functionalized multilayer micron-sized scroll structure comprising:
    a first layer, wherein the first layer comprises a nanosheet wherein the nanosheet comprises graphene oxide (GO),
    a second layer, wherein the second layer comprises titanium (Ti), and
    a third layer, wherein the third layer comprises platinum (Pt),
    wherein the first layer and the second layer roll spontaneously to form the multilayer micron-sized scroll structure, wherein the scroll structure is open at both ends and hollow in the center, and wherein the Pt layer comprises the innermost layer located within the interior of the scroll structure, and the GO layer comprises the outermost layer of the scroll structure.

2. The functionalized multilayer micron-sized scroll structure of claim 1, wherein the nanosheet is at least a single monolayer thick, and wherein the nanosheet layer is about 0.5 to 3.0 nm in thickness.

3. The functionalized multilayer micron-sized scroll structure of claim 1, further comprising at least one additional layer, wherein the second layer, the third layer, and the at least one additional layer are each at least about 1 nm thick.

4. The functionalized multilayer micron-sized scroll structure of claim 1, wherein the structure acts as a microjet engine in the presence of $H_2O_2$ due to a reaction between the Pt layer and the $H_2O_2$ to form $O_2$, and wherein the structure moves at a constant speed of about 85 to 975 $\mu m\ s^{-1}$.

* * * * *